US008143224B2

(12) United States Patent
Smith et al.

(10) Patent No.: US 8,143,224 B2
(45) Date of Patent: Mar. 27, 2012

(54) OXIDANT RESISTANT APOLIPOPROTEIN A-1 AND MIMETIC PEPTIDES

(75) Inventors: Jonathan D. Smith, Shaker Heights, OH (US); Stanley L. Hazen, Pepper Pike, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 627 days.

(21) Appl. No.: 12/256,822

(22) Filed: Oct. 23, 2008

(65) Prior Publication Data

US 2009/0149390 A1    Jun. 11, 2009

Related U.S. Application Data

(60) Provisional application No. 60/981,887, filed on Oct. 23, 2007.

(51) Int. Cl.
*A61K 38/10*     (2006.01)
*C07K 14/00*    (2006.01)

(52) U.S. Cl. ........ 514/21.2; 530/324; 530/350; 435/375

(58) Field of Classification Search .................... 514/13, 514/21.2; 530/326, 350, 324; 435/375
See application file for complete search history.

(56) References Cited

U.S. PATENT DOCUMENTS

| | | | |
|---|---|---|---|
| 4,376,110 A | 3/1983 | David et al. | |
| 4,816,397 A | 3/1989 | Boss et al. | |
| 4,816,567 A | 3/1989 | Cabilly et al. | |
| 4,946,778 A | 8/1990 | Ladner et al. | |
| 5,585,089 A | 12/1996 | Queen et al. | |
| 7,144,862 B2 | 12/2006 | Fogelman et al. | |
| 2002/0064820 A1* | 5/2002 | Dayer et al. ............... | 435/69.1 |

FOREIGN PATENT DOCUMENTS

WO    WO83/04053    11/1983

OTHER PUBLICATIONS

Boullier et al., "Interplay of Oxygen, Vitamin E., and Carotenoids in Radical Reactions Following Oxidation of Trp and Tyr Residues in Native HDL$_3$ Apolipoproteins. Comparison with LDL. A Time-Resolved Spectroscopic Analysis", *Biochemistry*, 46:5226-5237, May 1, 2007.
Datta et al., "Aromatic Residue Position on the Nonpolar Face of Class A Amphipathic Helical Peptides Determines Biological Activity", *The Journal of Biological Chemistry*, 279:26509-26517, Jun. 18, 2004.
Peng et al., "Apolipoprotein A-I Tryptophan Substitution Leads to Resistance to Myeloperoxidase-Mediated Loss of Function", *Arterioscler Thromb Vasc Biol.*, 28:2063-2070, Jul. 7, 2008.
Shao et al., "Myeloperoxidase Impairs ABCA1-Dependent Cholesterol Efflux through Methionine Oxidation and Site-Specific Tyrosine Chlorination of Apolipoprotein A-I", *Journal of Biological Chemistry*, 28:9001-9004, Apr. 7, 2006.

Davidson et al., "Structural Organization of the N-Terminal Domain of Apolipoprotein A-I: Stidues of Tryptophan Mutants", *Biochemistry* (1999), 38:14387-14395.
Gross et al., "A Novel Folding Intermediate State for Apolipoprotein A-I: Role of the Amino and Carboxy Termini", *Biophysical Journal* (2006), 90:1362-1370.
Nightingale et al., "Relative Reactivity of Lysine and Other Peptide-Bound Amino Acids to Oxidation by Hypochlorite", *Free Radical Biology & Medicine*, (2000), 29:425-433.
Sparks et al., "Effect of Cholesterol on the Charge and Structure of Apolipoprotein A-I in recombinant High Density Lipoprotein Particles", The Journal of Biological Chemistry, (1993), 268:23250-23257.
von Eckardestein et al., "Structural Analysis of Human Apolipoprotein A-I Variants", The Journal of Biological Chemistry (1990), 265:8610-8617.
Ansell, et al., "Inflammatory/Antiinflammatory Properties of High-Density Lipoprotein Distinguish ; Patients From Control Subjects Better Than High-Density Lipoprotein Cholesterol Levels and Are Favorably Affected by Simvastatin Treatment", *Circulation* 2003;108,2751-2756.
Bergt et al., "Lysine Residues Direct the Chlorination of Tyrosines in YXXK Motifs of Apolipoprotein A-1 When Hypochlorous Acid Oxidizes High Density Lipoprotein", The Journal of Biological Chemistry, vol. 1: 279, No. 9, issue of Februay 27, pp. 7856-7866, 2004.
Bergt et al., "The myeloperoxidase product hypochlorous acid oxidizes HDL in the human artery wall and impairs ABCA1-dependent cholesterol transport", 13032-13037, PNAS, Aug. 31, 2004, vol. 101, No, 35.
Brouilette, et al., "Structural models of human apoliprotein A-I a critical analysis and review", Biochimica et Biophysica Acta 1531 (2001) 4-46.
Brubaker et al., "Apolipoprotein A-I lysine modification: Effects on helical content, lipid binding and cholesterol acceptor activity", Biochimic et Biciphysica Acta 1761 (2006) 64-72.
Castelli, et al. "Incidence of Coronary Heart Disease and Lipoprotein Cholesterol Levels", JAMA, Nov. 28, 1986, vol. 256, No. 20.
Denis et al., "Molecular and Cellular Physiology of Apolipoprotein A-I Lipidation by the ATP-binding Cassette Transporter A1 (ABCA1)", The Journal of Biological Chemistry, vol. 279, No. 9, Issue of Feb. 27, pp, 7384-7394, 2004.
Garner et al., "Oxidation of High Density Lipoproteins", The Journal of Biological Chemistry, vol. 273, No. 11, Issue of Mar. 13, pp. 6088-6095, 1998.
Gordon et al., "High-Density lipoprotein cholesterol and cardiovascular disease. Four prospective American studies", *Circulation* 1989;79;8-15.
Harrison at al., "Studies on the Chlorinating Activity of Myeloperoxidase", The Journal of Biological Chemistry, vol. 251, No. 5, Issue Mar. 10, pp. 1371-1374, 1976.
Hazen et al., "3-Chlorotyrosine, a Specific Marker of Myeloperoxidase-catalyzed Oxidation, is Markedly Elevated in Low Density Lipoprotein Isolated from Human Atherosclerotic Intima", J. Clin. Invest. vol. 99, No. 9, May 1997, 2075-2081.

(Continued)

*Primary Examiner* — Chih-Min Kam
(74) *Attorney, Agent, or Firm* — Honigman Miller Schwartz and Cohn LLP; Fernando Alberdi; Jonathan P. O'Brien

(57) ABSTRACT

A purified polypeptide includes an ApoA1 mimetic or fragment thereof that are resistant to oxidation.

18 Claims, 12 Drawing Sheets

OTHER PUBLICATIONS

Jerlich et al., Kinetics of tryptophan oxidation in plasma lipoproteins by myeloperxidase-generated HOCI, *Eur. J. Biochem*, 267, 4137-4143 (2000)© FEBS 2000.

Kennedy et al.. "ABCG1 has a critical role in mediating cholesterol efflux to HDL and preventing cellular lipid accumulation", Cell Metabolism, Feb. 2005, vol. 1.

Mulya, et al , "Minimal Lipidation of Pre-β HDL by ABCA1 Results in Reduced Ability to Interact with ABCA1", *Arteriosler. Thromb. Vasc. Biol.* 200727;1828-1836.

Nissen et al., "Effect of Recombinant ApoA-I Milano Coronary Atherosclerosis in Patients with Acute Coronary Syndromes: A Randomized Controlled Trial", *JAMA*. 2003;290(17).2292-2300.

Oram et al., "ABCAi Is the cAMP-inducible Apoliprotein Receptor That Mediates Cholesterol Secretion from Macrophages", The Journal of Biological Chemistry, vol. 275, No. 44, issue of Nov. 3, pp. 34505-34511, 2000.

Peng, et al., "Tyrosine Modification is Not required for Myeloperoxidase-induced Loss of Apolipoprotein A-1 Functional Activities", The Journal of Biological Chemistry, vol. 280, No. 40, pp. 33775-33784, Oct. 7, 2005.

Pennathur et al., "Human Atherosclerotic Intima and Blood of Patients with Established Coroney Artery Disease Contain High Density Lipoprotein Damaged by Reactive Nitrogen Species", The Journal of Biological Chemistry, vol. 279, No, 41, issue of Oct. 8, pp. 42977-42983, 2004.

Ryan, et al., "Optimized bacterial expression of human apoliprotein A-I" Protein Expression and Purification 27 (2003) 98-103.

Segrest, et al, "A Detailed Molecular Belt Model for Apoliprotein A-I in Discoidal High Density Lipoprotein", The Journal of Biological Chemistry, vol. 274, No. 45, Issue of Nov. 5, pp. 31755-31758, 1999.

Shao et al., "Myeloperoxidase Impairs ABCA-1dependent Cholesterol Efflux through Methionine Oxidation and Site-Specific Tyrosine Chlorination of Apolipoprotein A-I", The Journal of Biological Chemistry vol. 281, No. 14, pp. 9001-9004, Apr. 7, 2006.

Shao, et al., "Tyrosine 192 in Apolipoprotein A-1 is the Major Site of Nitration and Chlorination by Myeloperoxidase, but Only Chlorination Markedly Impairs ABSA1-dependent Cholesterol Transport", The Journal of Biological Chemistry, vol. 280, No. 7, issue of Feb. 18, pp. 5983-5993, 2005.

Smith et al., "ABCA1 mediates concurrent cholesterol and phospholipid efflux to apolipoprotein A-I", Journal of Lipid Research, vol. 45, 2004.

Smith et al., "Cyclic AAMP Induces Apolipoprotein E Binding Activity and Promotes Cholesterol Efflux from a Macrophage Cell Line to Apolipoprotein Acceptors", Journal of Biological Chemistry, vol. 271, No. 48, Issue of Nov. 29, pp. 30647-30655, 1996.

Wang et al, "Macrophage ABCA1 and ABCG1, but not SR-BI, promote macrophage reverse cholesterol transport in vivo", *J. Clin. Invest.* 117:2216-2224(2007).

Wimley et al., "Experimentally determined hydrophobicity scale for proteins at membrane interfaces", nature structural biology vol. 3 No. 10 Oct. 1996.

Zheng at at., "Apolipoprotein A-1 is a selective target for myeloperoxidase-catalyzed oxidation and functional impairment in subjects with cardiovascular disease", J. Clin. Invest. 114:529-541 (2004).

Zheng et al., "Localization of Nitration and Chlorination Sites on A-I Catalyzed by Myeloperoxidase in Human Atheroma and Associated Oxidative Impairment in ABCA1-Dependent Cholesterol Efflux from Macrophages", *J. Biolgical Chemistry*, 280:38-47 (2005).

\* cited by examiner

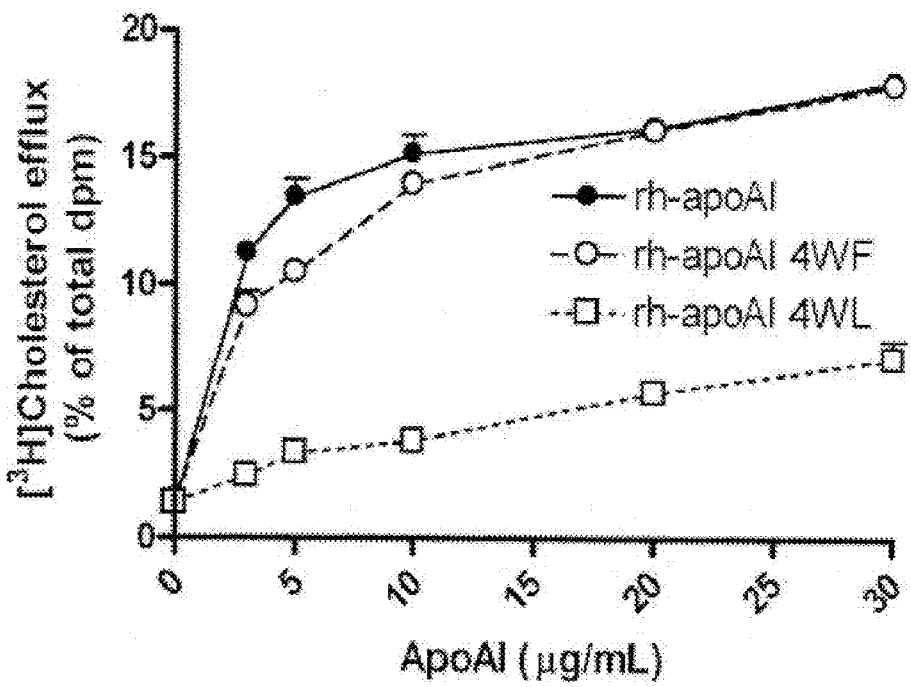
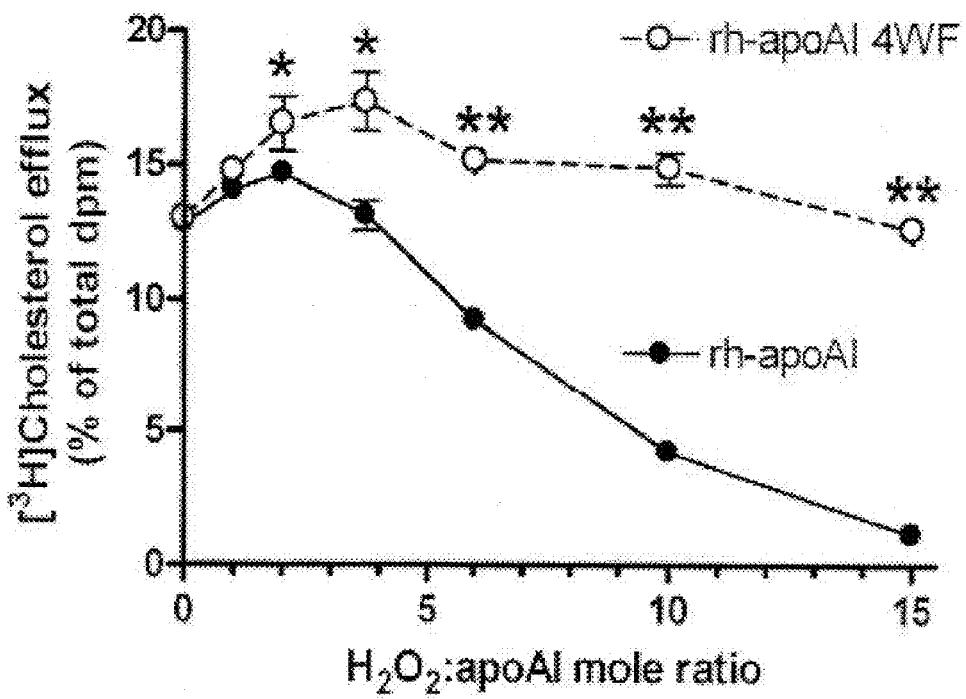
Figs. 5A-B

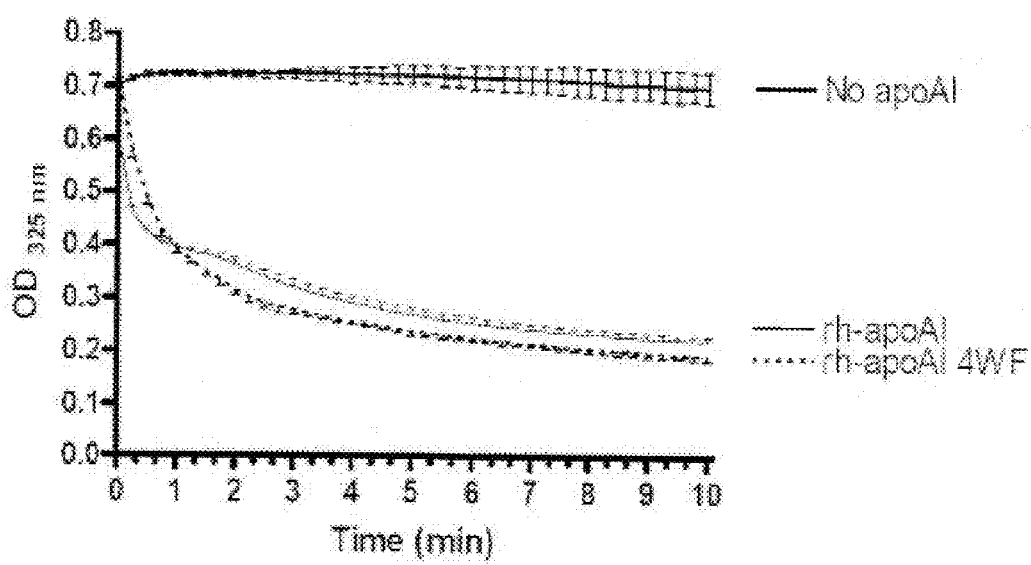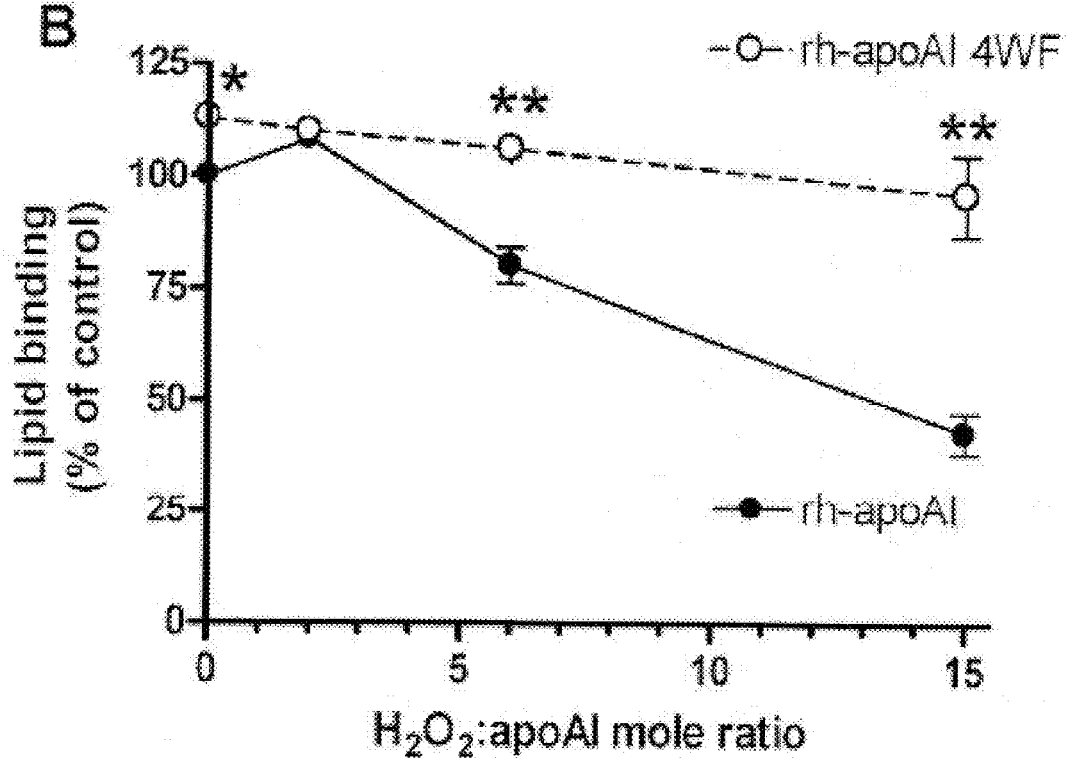
Figs. 7A-B

A

SEQUENCE LISTING

```
<160> NUMBER OF SEQ ID NOS: 76

<210> SEQ ID NO 1
<211> LENGTH: 243
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is tryptophan or an oxidant resistant amino
      acid
<220> FEATURE:
<221> NAME/KEY: MISC_FEATURE
<222> LOCATION: (50)..(50)
<223> OTHER INFORMATION: Xaa is tryptophan or an oxidant resistant amino
      acid
<220> FEATURE:
<221> NAME/KEY: MISC_FEATURE
<222> LOCATION: (72)..(72)
<223> OTHER INFORMATION: Xaa is tryptophan or an oxidant resistant amino
      acid
<220> FEATURE:
<221> NAME/KEY: MISC_FEATURE
<222> LOCATION: (108)..(108)
<223> OTHER INFORMATION: Xaa is tryptophan or an oxidant resistant amino
      acid

<400> SEQUENCE: 1

Asp Glu Pro Pro Gln Ser Pro Xaa Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Xaa Asp Ser Val Thr Ser Thr Phe Ser Lys Leu Arg Glu Gln Leu
    50                  55                  60

Gly Pro Val Thr Gln Glu Phe Xaa Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Xaa Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160
```

```
Thr His Leu Ala Pro Tyr Ser Asp Glu Leu Arg Gln Arg Leu Ala Ala
            165                 170                 175

Arg Leu Glu Ala Leu Lys Glu Asn Gly Ala Arg Leu Ala Glu Tyr
        180                 185                 190

His Ala Lys Ala Thr Glu His Leu Ser Thr Leu Ser Lys Ala Lys
        195                 200                 205

Pro Ala Leu Glu Asp Leu Arg Gln Gly Leu Leu Pro Val Leu Glu Ser
        210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 243
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa is tryptophan or an oxidant resistant amino
      acid
<220> FEATURE:
<221> NAME/KEY: MISC_FEATURE
<222> LOCATION: (32)..(32)
<223> OTHER INFORMATION: Xaa is tryptophan or an oxidant resistant amino
      acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: MISC_FEATURE
<222> LOCATION: (74)..(74)
<223> OTHER INFORMATION: Xaa is tryptophan or an oxidant resistant amino
      acid
<220> FEATURE:
<221> NAME/KEY: MISC_FEATURE
<222> LOCATION: (96)..(96)
<223> OTHER INFORMATION: Xaa is tryptophan or an oxidant resistant amino
      acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: MISC_FEATURE
<222> LOCATION: (132)..(132)
<223> OTHER INFORMATION: Xaa is tryptophan or an oxidant resistant amino
      acid

<400> SEQUENCE: 2

Asp Glu Pro Pro Gln Ser Pro Xaa Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Xaa Asp Ser Val Thr Ser Thr Phe Ser Lys Leu Arg Glu Gln Leu
    50                  55                  60

Gly Pro Val Thr Gln Glu Phe Xaa Asp Asn Leu Glu Lys Glu Thr Glu
65                  70                  75                  80
```

-continued

```
Gly Leu Arg Gln Glu Met Ser Lys Asp Leu Glu Val Lys Ala Lys
                 85                  90                  95

Val Gln Pro Tyr Leu Asp Asp Phe Gln Lys Lys Xaa Gln Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 3
<211> LENGTH: 243
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: Xaa is tryptophan or an oxidant resistant amino
      acid
<220> FEATURE:
<221> NAME/KEY: MISC_FEATURE
<222> LOCATION: (32)..(32)
<223> OTHER INFORMATION: Xaa is tryptophan or an oxidant resistant amino
      acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: MISC_FEATURE
<222> LOCATION: (74)..(74)
<223> OTHER INFORMATION: Xaa is tryptophan or an oxidant resistant amino
      acid
<220> FEATURE:
<221> NAME/KEY: MISC_FEATURE
<222> LOCATION: (96)..(96)
<223> OTHER INFORMATION: Xaa is tryptophan or an oxidant resistant amino
      acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: MISC_FEATURE
<222> LOCATION: (132)..(132)
<223> OTHER INFORMATION: Xaa is tryptophan or an oxidant resistant amino
      acid
```

```
<400> SEQUENCE: 3

Asp Glu Pro Pro Gln Ser Pro Xaa Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Xaa Asp Ser Val Thr Ser Thr Phe Ser Lys Leu Arg Glu Gln Leu
50                  55                  60

Gly Pro Val Thr Gln Glu Phe Xaa Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Xaa Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 4
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X is an oxidant resistant amino acid
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 4

Asp Xaa Leu Lys Ala Phe Tyr Asp Lys Val Ala Glu Lys Leu Lys Glu
1               5                   10                  15

Ala Phe

<210> SEQ ID NO 5
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid
```

<400> SEQUENCE: 5

Asp Xaa Phe Lys Ala Phe Tyr Asp Lys Val Ala Glu Lys Leu Lys Glu
1               5                   10                  15

Ala Phe

<210> SEQ ID NO 6
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 6

Asp Xaa Leu Lys Ala Phe Tyr Asp Lys Val Ala Glu Lys Phe Lys Glu
1               5                   10                  15

Ala Phe

<210> SEQ ID NO 7
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 7

Asp Xaa Phe Lys Ala Phe Tyr Asp Lys Val Ala Glu Lys Phe Lys Glu
1               5                   10                  15

Ala Phe

<210> SEQ ID NO 8
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 8

Asp Xaa Leu Lys Ala Phe Tyr Asp Lys Val Phe Glu Lys Phe Lys Glu
1               5                   10                  15

Phe Phe

<210> SEQ ID NO 9
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 9

Asp Xaa Leu Lys Ala Phe Tyr Asp Lys Phe Phe Glu Lys Phe Lys Glu
1               5                   10                  15

Phe Phe

<210> SEQ ID NO 10
<211> LENGTH: 18
<212> TYPE: PRT
<213> ORGANISM: Homo sapiens

```
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 10

Asp Xaa Phe Lys Ala Phe Tyr Asp Lys Phe Phe Glu Lys Phe Lys Glu
 1               5                  10                  15

Phe Phe

<210> SEQ ID NO 11
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 11

Asp Xaa Leu Lys Ala Phe Tyr Asp Lys Val Phe Glu Lys Phe Lys Glu
 1               5                  10                  15

Ala Phe

<210> SEQ ID NO 12
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant acid

<400> SEQUENCE: 12

Asp Xaa Leu Lys Ala Phe Tyr Asp Lys Val Phe Glu Lys Phe Lys Glu
 1               5                  10                  15

Ala Phe

<210> SEQ ID NO 13
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 13

Asp Xaa Leu Lys Ala Phe Tyr Asp Lys Val Phe Glu Lys Leu Lys Glu
 1               5                  10                  15

Phe Phe

<210> SEQ ID NO 14
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 14

Asp Xaa Leu Lys Ala Phe Tyr Asp Lys Val Ala Glu Lys Phe Lys Glu
 1               5                  10                  15

Phe Phe
```

<210> SEQ ID NO 15
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 15

Asp Xaa Leu Lys Ala Phe Tyr Asp Lys Val Phe Glu Lys Phe Lys Glu
1               5                   10                  15

Phe Phe

<210> SEQ ID NO 16
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 16

Glu Xaa Leu Lys Leu Phe Tyr Glu Lys Val Leu Glu Lys Phe Lys Glu
1               5                   10                  15

Ala Phe

<210> SEQ ID NO 17
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 17

Glu Xaa Leu Lys Ala Phe Tyr Asp Lys Val Ala Glu Lys Phe Lys Glu
1               5                   10                  15

Ala Phe

<210> SEQ ID NO 18
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 18

Glu Xaa Leu Lys Ala Phe Tyr Asp Lys Val Ala Glu Lys Leu Lys Glu
1               5                   10                  15

Phe Phe

<210> SEQ ID NO 19
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

```
<400> SEQUENCE: 19

Glu Xaa Leu Lys Ala Phe Tyr Asp Lys Val Phe Glu Lys Phe Lys Glu
1               5                   10                  15

Ala Phe

<210> SEQ ID NO 20
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 20

Glu Xaa Leu Lys Ala Phe Tyr Asp Lys Val Phe Glu Lys Leu Lys Glu
1               5                   10                  15

Phe Phe

<210> SEQ ID NO 21
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 21

Glu Xaa Leu Lys Ala Phe Tyr Asp Lys Val Ala Glu Lys Phe Lys Glu
1               5                   10                  15

Phe Phe

<210> SEQ ID NO 22
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 22

Glu Xaa Leu Lys Ala Phe Tyr Asp Lys Val Phe Glu Lys Phe Lys Glu
1               5                   10                  15

Phe Phe

<210> SEQ ID NO 23
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 23

Asp Xaa Leu Lys Ala Leu Tyr Asp Lys Val Ala Glu Lys Leu Lys Glu
1               5                   10                  15

Ala Leu

<210> SEQ ID NO 24
<211> LENGTH: 18
<212> TYPE: PRT
<213> ORGANISM: Homo sapiens
```

```
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 24

Asp Xaa Phe Lys Ala Phe Tyr Glu Lys Val Ala Glu Lys Leu Lys Glu
1               5                   10                  15

Phe Phe

<210> SEQ ID NO 25
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 25

Asp Xaa Phe Lys Ala Phe Tyr Glu Lys Phe Phe Glu Lys Phe Lys Glu
1               5                   10                  15

Phe Phe

<210> SEQ ID NO 26
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 26

Glu Xaa Leu Lys Ala Leu Tyr Glu Lys Val Ala Glu Lys Leu Lys Glu
1               5                   10                  15

Ala Leu

<210> SEQ ID NO 27
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 27

Glu Xaa Leu Lys Ala Phe Tyr Glu Lys Val Ala Glu Lys Leu Lys Glu
1               5                   10                  15

Ala Phe

<210> SEQ ID NO 28
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 28

Glu Xaa Phe Lys Ala Phe Tyr Glu Lys Val Ala Glu Lys Leu Lys Glu
1               5                   10                  15

Phe Phe
```

```
<210> SEQ ID NO 29
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 29

Glu Xaa Leu Lys Ala Phe Tyr Glu Lys Val Phe Glu Lys Phe Lys Glu
1               5                   10                  15

Phe Phe

<210> SEQ ID NO 30
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 30

Glu Xaa Leu Lys Ala Phe Tyr Glu Lys Phe Phe Glu Lys Phe Lys Glu
1               5                   10                  15

Phe Phe

<210> SEQ ID NO 31
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 31

Glu Xaa Phe Lys Ala Phe Tyr Glu Lys Phe Phe Glu Lys Phe Lys Glu
1               5                   10                  15

Phe Phe

<210> SEQ ID NO 32
<211> LENGTH: 18
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is tryptophan or an oxidant resistant amino
      acid
<220> FEATURE:
<221> NAME/KEY: MISC_FEATURE
<222> LOCATION: (18)..(18)
<223> OTHER INFORMATION: Xaa is tryptophan or an oxidant resistant amino
      acid

<400> SEQUENCE: 32

Asp Phe Leu Lys Ala Xaa Tyr Asp Lys Val Ala Glu Lys Leu Lys Glu
1               5                   10                  15

Ala Xaa

<210> SEQ ID NO 33
<211> LENGTH: 18
<212> TYPE: PRT
<213> ORGANISM: Homo sapiens
```

```
<220> FEATURE:
<221> NAME/KEY: MISC_FEATURE
<222> LOCATION: (6)..(6)
<223> OTHER INFORMATION: Xaa is tryptophan or an oxidant resistant amino
      acid
<220> FEATURE:
<221> NAME/KEY: MISC_FEATURE
<222> LOCATION: (18)..(18)
<223> OTHER INFORMATION: Xaa is tryptophan or an oxidant resistant amino
      acid

<400> SEQUENCE: 33

Glu Phe Leu Lys Ala Xaa Tyr Glu Lys Val Ala Glu Lys Leu Lys Glu
1               5                   10                  15

Ala Xaa

<210> SEQ ID NO 34
<211> LENGTH: 18
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is tryptophan or an oxidant resistant amino
      acid
<220> FEATURE:
<221> NAME/KEY: MISC_FEATURE
<222> LOCATION: (6)..(6)
<223> OTHER INFORMATION: Xaa is tryptophan or an oxidant resistant amino
      acid
<220> FEATURE:
<221> NAME/KEY: MISC_FEATURE
<222> LOCATION: (17)..(17)
<223> OTHER INFORMATION: Xaa is tryptophan or an oxidant resistant amino
      acid
<220> FEATURE:
<221> NAME/KEY: MISC_FEATURE
<222> LOCATION: (18)..(18)

<400> SEQUENCE: 34

Asp Phe Xaa Lys Ala Xaa Tyr Asp Lys Val Ala Glu Lys Leu Lys Glu
1               5                   10                  15

Xaa Xaa

<210> SEQ ID NO 35
<211> LENGTH: 18
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is tryptophan or oxidant resistant amino
      acid
<220> FEATURE:
<221> NAME/KEY: MISC_FEATURE
<222> LOCATION: (6)..(6)
<223> OTHER INFORMATION: Xaa is tryptophan or oxidant resistant amino
      acid
<220> FEATURE:
<221> NAME/KEY: MISC_FEATURE
<222> LOCATION: (17)..(17)
<223> OTHER INFORMATION: Xaa is tryptophan or oxidant resistant amino
      acid
<220> FEATURE:
<221> NAME/KEY: MISC_FEATURE
<222> LOCATION: (18)..(18)
<223> OTHER INFORMATION: Xaa is tryptophan or oxidant resistant amino
      acid
```

<400> SEQUENCE: 35

Glu Phe Xaa Lys Ala Xaa Tyr Glu Lys Val Ala Glu Lys Leu Lys Glu
1               5                   10                  15

Xaa Xaa

<210> SEQ ID NO 36
<211> LENGTH: 18
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is an oxidant resistant amino acid

<400> SEQUENCE: 36

Asp Lys Leu Lys Ala Phe Tyr Asp Lys Val Phe Glu Xaa Ala Lys Glu
1               5                   10                  15

Ala Phe

<210> SEQ ID NO 37
<211> LENGTH: 18
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is an oxidant resistant amino acid

<400> SEQUENCE: 37

Asp Lys Xaa Lys Ala Val Tyr Asp Lys Phe Ala Glu Ala Phe Lys Glu
1               5                   10                  15

Phe Leu

<210> SEQ ID NO 38
<211> LENGTH: 18
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is an oxidant resistant amino acid

<400> SEQUENCE: 38

Glu Lys Leu Lys Ala Phe Tyr Glu Lys Val Phe Glu Xaa Ala Lys Glu
1               5                   10                  15

Ala Phe

<210> SEQ ID NO 39
<211> LENGTH: 18
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is an oxidant resistant amino acid

<400> SEQUENCE: 39

Glu Lys Xaa Lys Ala Val Tyr Glu Lys Phe Ala Glu Ala Phe Lys Glu
1               5                   10                  15

Phe Leu

<210> SEQ ID NO 40
<211> LENGTH: 18
<212> TYPE: PRT
<213> ORGANISM: Homo sapiens

```
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 40

Asp Xaa Leu Lys Ala Phe Val Asp Lys Phe Ala Glu Lys Phe Lys Glu
1               5                   10                  15

Ala Tyr

<210> SEQ ID NO 41
<211> LENGTH: 18
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is an oxidant resistant amino acid

<400> SEQUENCE: 41

Glu Lys Xaa Lys Ala Val Tyr Glu Lys Phe Ala Glu Ala Phe Lys Glu
1               5                   10                  15

Phe Leu

<210> SEQ ID NO 42
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 42

Asp Xaa Leu Lys Ala Phe Val Tyr Asp Lys Val Phe Lys Leu Lys Glu
1               5                   10                  15

Phe Phe

<210> SEQ ID NO 43
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 43

Glu Xaa Leu Lys Ala Phe Val Tyr Glu Lys Val Phe Lys Leu Lys Glu
1               5                   10                  15

Phe Phe

<210> SEQ ID NO 44
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 44

Asp Xaa Leu Arg Ala Phe Tyr Asp Lys Val Ala Glu Lys Leu Lys Glu
1               5                   10                  15

Ala Phe
```

```
<210> SEQ ID NO 45
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 45

Glu Xaa Leu Arg Ala Phe Tyr Glu Lys Val Ala Glu Lys Leu Lys Glu
1               5                   10                  15

Ala Phe

<210> SEQ ID NO 46
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 46

Asp Xaa Leu Lys Ala Phe Tyr Asp Arg Val Ala Glu Lys Leu Lys Glu
1               5                   10                  15

Ala Phe

<210> SEQ ID NO 47
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 47

Glu Xaa Leu Lys Ala Phe Tyr Glu Arg Val Ala Glu Lys Leu Lys Glu
1               5                   10                  15

Ala Phe

<210> SEQ ID NO 48
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 48

Asp Xaa Leu Lys Ala Phe Tyr Asp Lys Val Ala Glu Arg Leu Lys Glu
1               5                   10                  15

Ala Phe

<210> SEQ ID NO 49
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid
```

-continued

```
<400> SEQUENCE: 49

Glu Xaa Leu Lys Ala Phe Tyr Glu Lys Val Ala Glu Arg Leu Lys Glu
1               5                   10                  15

Ala Phe

<210> SEQ ID NO 50
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 50

Asp Xaa Leu Lys Ala Phe Tyr Asp Lys Val Ala Glu Lys Leu Arg Glu
1               5                   10                  15

Ala Phe

<210> SEQ ID NO 51
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 51

Glu Xaa Leu Lys Ala Phe Tyr Glu Lys Val Ala Glu Lys Leu Arg Glu
1               5                   10                  15

Ala Phe

<210> SEQ ID NO 52
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 52

Asp Xaa Leu Lys Ala Phe Tyr Asp Arg Val Ala Glu Arg Leu Lys Glu
1               5                   10                  15

Ala Phe

<210> SEQ ID NO 53
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 53

Glu Xaa Leu Lys Ala Phe Tyr Glu Arg Val Ala Glu Arg Leu Lys Glu
1               5                   10                  15

Ala Phe

<210> SEQ ID NO 54
<211> LENGTH: 18
<212> TYPE: PRT
<213> ORGANISM: Homo sapiens
```

```
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 54

Asp Xaa Leu Arg Ala Phe Tyr Asp Lys Val Ala Glu Lys Leu Arg Glu
1               5                   10                  15

Ala Phe

<210> SEQ ID NO 55
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 55

Glu Xaa Leu Arg Ala Phe Tyr Glu Lys Val Ala Glu Lys Leu Arg Glu
1               5                   10                  15

Ala Phe

<210> SEQ ID NO 56
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 56

Asp Xaa Leu Arg Ala Phe Tyr Asp Arg Val Ala Glu Lys Leu Lys Glu
1               5                   10                  15

Ala Phe

<210> SEQ ID NO 57
<211> LENGTH: 17
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is an oxidant resistant amino acid

<400> SEQUENCE: 57

Xaa Leu Arg Ala Phe Tyr Glu Arg Val Ala Glu Lys Leu Lys Glu Ala
1               5                   10                  15

Phe

<210> SEQ ID NO 58
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 58

Asp Xaa Leu Lys Ala Phe Tyr Asp Lys Val Ala Glu Arg Leu Arg Glu
1               5                   10                  15

Ala Phe
```

```
<210> SEQ ID NO 59
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 59

Glu Xaa Leu Lys Ala Phe Tyr Glu Lys Val Ala Glu Arg Leu Arg Glu
1               5                   10                  15

Ala Phe

<210> SEQ ID NO 60
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 60

Asp Xaa Leu Arg Ala Phe Tyr Asp Lys Val Ala Glu Arg Leu Lys Glu
1               5                   10                  15

Ala Phe

<210> SEQ ID NO 61
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is an oxidant resistant amino acid

<400> SEQUENCE: 61

Glu Xaa Leu Arg Ala Phe Tyr Glu Lys Val Ala Glu Arg Leu Lys Glu
1               5                   10                  15

Ala Phe

<210> SEQ ID NO 62
<211> LENGTH: 37
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is tryptophan or an oxidant resistant amino
      acid
<220> FEATURE:
<221> NAME/KEY: MISC_FEATURE
<222> LOCATION: (21)..(21)
<223> OTHER INFORMATION: Xaa is tryptophan or an oxidant resistant amino
      acid

<400> SEQUENCE: 62

Asp Xaa Leu Lys Ala Phe Tyr Asp Lys Val Ala Glu Lys Leu Lys Glu
1               5                   10                  15

Ala Phe Pro Asp Xaa Leu Lys Ala Phe Tyr Asp Lys Val Ala Glu Lys
            20                  25                  30

Leu Lys Glu Ala Phe
        35
```

```
<210> SEQ ID NO 63
<211> LENGTH: 37
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is tryptophan or an oxidant resistant amino
      acid
<220> FEATURE:
<221> NAME/KEY: MISC_FEATURE
<222> LOCATION: (21)..(21)
<223> OTHER INFORMATION: Xaa is tryptophan or an oxidant resistant amino
      acid

<400> SEQUENCE: 63

Asp Xaa Leu Lys Ala Phe Tyr Asp Lys Val Ala Glu Lys Leu Lys Glu
1               5                   10                  15

Phe Phe Pro Asp Xaa Leu Lys Ala Phe Tyr Asp Lys Val Ala Glu Lys
            20                  25                  30

Leu Lys Glu Phe Phe
        35

<210> SEQ ID NO 64
<211> LENGTH: 37
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is tryptophan or an oxidant resistant amino
      acid
<220> FEATURE:
<221> NAME/KEY: MISC_FEATURE
<222> LOCATION: (21)..(21)
<223> OTHER INFORMATION: Xaa is tryptophan or an oxidant resistant amino
      acid

<400> SEQUENCE: 64

Asp Xaa Phe Lys Ala Phe Tyr Asp Lys Val Ala Glu Lys Leu Lys Glu
1               5                   10                  15

Ala Phe Pro Asp Xaa Phe Lys Ala Phe Tyr Asp Lys Val Ala Glu Lys
            20                  25                  30

Leu Lys Glu Ala Phe
        35

<210> SEQ ID NO 65
<211> LENGTH: 37
<212> TYPE: PRT
<213> ORGANISM: Homo sapiens
<220> FEATURE:
<221> NAME/KEY: MISC_FEATURE
<222> LOCATION: (13)..(13)
<223> OTHER INFORMATION: Xaa is tryptophan or an oxidant resistant amino
      acid
<220> FEATURE:
<221> NAME/KEY: MISC_FEATURE
<222> LOCATION: (22)..(22)
<223> OTHER INFORMATION: Xaa is tryptophan or an oxidant resistant amino
      acid
<220> FEATURE:
<221> NAME/KEY: misc_feature
<222> LOCATION: (32)..(32)
<223> OTHER INFORMATION: Xaa can be any naturally occurring amino acid
```

```
<400> SEQUENCE: 65

Asp Lys Leu Lys Ala Phe Tyr Asp Lys Val Phe Glu Xaa Ala Lys Glu
1               5                   10                  15

Ala Phe Pro Asp Lys Leu Lys Ala Phe Tyr Asp Lys Val Phe Glu Xaa
            20                  25                  30

Leu Lys Glu Ala Phe
            35

<210> SEQ ID NO 66
<211> LENGTH: 37
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is tryptophan or an oxidant resistant amino
      acid
<220> FEATURE:
<221> NAME/KEY: MISC_FEATURE
<222> LOCATION: (22)..(22)
<223> OTHER INFORMATION: Xaa is tryptophan or an oxidant resistant amino
      acid

<400> SEQUENCE: 66

Asp Lys Xaa Lys Ala Val Tyr Asp Lys Phe Ala Glu Ala Phe Lys Glu
1               5                   10                  15

Phe Leu Pro Asp Lys Xaa Lys Ala Val Tyr Asp Lys Phe Ala Glu Ala
            20                  25                  30

Phe Lys Glu Phe Leu
            35

<210> SEQ ID NO 67
<211> LENGTH: 37
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is tryptophan or an oxidant resistant amino
      acid
<220> FEATURE:
<221> NAME/KEY: MISC_FEATURE
<222> LOCATION: (21)..(21)
<223> OTHER INFORMATION: Xaa is tryptophan or an oxidant resistant amino
      acid

<400> SEQUENCE: 67

Asp Xaa Phe Lys Ala Phe Tyr Asp Lys Val Ala Glu Lys Phe Lys Glu
1               5                   10                  15

Ala Phe Pro Asp Xaa Phe Lys Ala Phe Tyr Asp Lys Val Ala Glu Lys
            20                  25                  30

Phe Lys Glu Ala Phe
            35

<210> SEQ ID NO 68
<211> LENGTH: 37
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is tryptophan or an oxidant resistant amino
      acid
<220> FEATURE:
<221> NAME/KEY: MISC_FEATURE
<222> LOCATION: (21)..(21)
<223> OTHER INFORMATION: Xaa is tryptophan or an oxidant resistant amino
      acid
```

-continued

```
<400> SEQUENCE: 68

Asp Xaa Leu Lys Ala Phe Val Tyr Asp Lys Val Phe Lys Leu Lys Glu
1               5                   10                  15

Phe Phe Pro Asp Xaa Leu Lys Ala Phe Val Tyr Asp Lys Val Phe Lys
                20                  25                  30

Leu Lys Glu Phe Phe
            35

<210> SEQ ID NO 69
<211> LENGTH: 37
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is tryptophan or an oxidant resistant amino
      acid
<220> FEATURE:
<221> NAME/KEY: MISC_FEATURE
<222> LOCATION: (21)..(21)
<223> OTHER INFORMATION: Xaa is tryptophan or an oxidant resistant amino
      acid

<400> SEQUENCE: 69

Asp Xaa Leu Lys Ala Phe Tyr Asp Lys Phe Ala Glu Lys Phe Lys Glu
1               5                   10                  15

Phe Phe Pro Asp Xaa Leu Lys Ala Phe Tyr Asp Lys Phe Ala Glu Lys
                20                  25                  30

Phe Lys Glu Phe Phe
            35

<210> SEQ ID NO 70
<211> LENGTH: 10
<212> TYPE: PRT
<213> ORGANISM: Homo sapiens

<400> SEQUENCE: 70

Asp Glu Pro Pro Gln Ser Pro Trp Asp Arg
1               5                   10

<210> SEQ ID NO 71
<211> LENGTH: 14
<212> TYPE: PRT
<213> ORGANISM: Homo sapiens

<400> SEQUENCE: 71

Leu Leu Asp Asn Trp Asp Ser Val Thr Ser Thr Phe Ser Lys
1               5                   10

<210> SEQ ID NO 72
<211> LENGTH: 16
<212> TYPE: PRT
<213> ORGANISM: Homo sapiens

<400> SEQUENCE: 72

Glu Gln Leu Gly Pro Val Thr Gln Glu Phe Trp Asp Asn Leu Glu Lys
1               5                   10                  15

<210> SEQ ID NO 73
<211> LENGTH: 9
<212> TYPE: PRT
<213> ORGANISM: Homo sapiens
```

```
<400> SEQUENCE: 73

Trp Gln Glu Glu Met Glu Leu Tyr Arg
1               5

<210> SEQ ID NO 74
<211> LENGTH: 9
<212> TYPE: PRT
<213> ORGANISM: Homo sapiens

<400> SEQUENCE: 74

Trp Gln Glu Glu Met Glu Leu Tyr Arg
1               5

<210> SEQ ID NO 75
<211> LENGTH: 9
<212> TYPE: PRT
<213> ORGANISM: Homo sapiens

<400> SEQUENCE: 75

Leu Ser Pro Leu Gly Glu Glu Met Arg
1               5

<210> SEQ ID NO 76
<211> LENGTH: 18
<212> TYPE: PRT
<213> ORGANISM: Homo sapiens

<400> SEQUENCE: 76

Asp Trp Phe Lys Ala Phe Tyr Asp Lys Val Ala Glu Lys Phe Lys Glu
1               5                   10                  15

Ala Phe
```

OXIDANT RESISTANT APOLIPOPROTEIN A-1 AND MIMETIC PEPTIDES

RELATED APPLICATION

This application claims priority from U.S. Provisional Application No. 60/981,887, filed Oct. 23, 2007, the subject matter which is incorporated herein by reference.

BACKGROUND OF THE INVENTION

Circulating cholesterol is carried by plasma lipoproteins. Lipoproteins are particles of lipid and protein that transport lipids in the blood. Low-density lipoproteins (LDL) and high-density lipoproteins (HDL) are the major cholesterol carriers. LDL is believed to be responsible for the delivery of cholesterol from the liver to extrahepatic tissues in the body.

The term "reverse cholesterol transport" (RCT) describes the transport of cholesterol from extrahepatic tissues to the liver where it is catabolized and eliminated. It is believed that plasma HDL particles play a major role in the reverse transport process, acting as scavengers of tissue cholesterol. RCT consists mainly of three steps: (a) cholesterol efflux, the initial removal of cholesterol from various pools of peripheral cells; (b) cholesterol esterification by the action of lecithin: cholesterol acyltransferase (LCAT), preventing a re-entry of effluxed cholesterol into cells; and (c) uptake/delivery of HDL cholesteryl ester to liver cells.

High levels of HDL and apolipoprotien A-1 (ApoA1), the major HDL protein, have long been associated with decreased risk for cardiovascular disease. ApoA1 is a single polypeptide chain with 243 amino acid residues of known primary amino acid sequence (Brewer et al., (1978) *Biochem. Biophys. Res. Commun.* 80: 623-630). ApoA1 acts as an acceptor of cellular cholesterol in the reverse cholesterol transport by mediating cholesterol efflux from cells.

Each HDL particle contains at least one copy (and usually two to four copies) of ApoA1. ApoA1 is synthesized in humans in the form of a preproapolipoprotein of 267 residues by the liver and small intestine which is secreted as a propro-tein that is rapidly cleaved by the action of a calcium-dependent protease to generate a mature 243 amino acid polypeptide and secreted into the plasma. Apo A1 has been postulated to possess eight tandem repeating 22 mer sequences and two 11 mer sequences, most of which have the potential to form class A amphipathic helical structures (Segrest et al. (1974) *FEBS Lett.* 38::247-253). Characteristics of the class A amphipathic helix include the presence of positively charged residues at the polar-nonpolar interface and negatively charged residues at the center of the polar face (Segrest et al. (1974) *FEBS Lett.* 38: 247-253; Segrest et al. (1990) *Proteins: Structure, Function, and Genetics* 8: 103-117).

ApoA1 forms three types of stable complexes with lipids: small, lipid-poor complexes referred to as pre-beta-1 HDL; flattened discoidal particles containing polar lipids (phospholipid and cholesterol) referred to as pre-beta-2 HDL; and spherical particles containing both polar and nonpolar lipids, referred to as spherical or mature HDL ($HDL_3$ and $HDL_2$). Most HDL in the circulating population contain both ApoA1 and ApoAII (the second major HDL protein) and are referred to as the A1/AII-HDL fraction of HDL. However, the fraction of HDL containing only ApoA1 (referred to herein as the A1-HDL fraction) appear to be more effective in RCT. Certain epidemiologic studies support the hypothesis that the A1-HDL fraction is anti-atherogenic. (Parra et al., 1992, Arterioscler. Thromb. 12:701-707; Decossin et al., 1997, Eur. J. Clin. Invest. 27:299-307).

The evidence linking elevated serum cholesterol to coronary heart disease is overwhelming. For example, atherosclerosis is a slowly progressive disease characterized by the accumulation of cholesterol within the arterial wall. Compelling evidence supports the concept that lipids deposited in atherosclerotic lesions are derived primarily from plasma LDL; thus, LDLs have popularly become known as "bad cholesterol". In contrast, HDL serum levels correlate inversely with coronary heart disease, and as such are regarded as a negative risk factor. It is hypothesized that high levels of plasma HDL are not only protective against coronary artery disease, but may actually induce regression of atherosclerotic plaques (e.g. Badimon et al., 1992, Circulation 86(Suppl. III):86-94). Thus, HDL has popularly become known as the "good cholesterol".

SUMMARY OF THE INVENTION

The present invention relates to a new ApoA1 mimetic that is capable of promoting cholesterol efflux from lipid loaded cells. The new ApoA1 mimetic has an amino acid sequence that is substantially similar to at least a portion of the amino acid sequence of native ApoA1 or a prior mimetic of the ApoA1 that contains at least one tryptophan and is capable of promoting cholesterol efflux from lipid loaded cells. The new ApoA1 mimetic, unlike native ApoA1 or prior mimetics of ApoA1, has at least one tryptophan in the amino acid sequence substituted with an oxidant resistant amino acid. The new ApoA1 mimetic can include an amino acid sequence of, for example, a tryptophan containing ApoA1 fragment, native ApoA1, ApoA1 fusion protein, ApoA1 chimeric protein, a truncated ApoA1 protein, or a prior mimetic of an ApoA1 polypeptide, wherein at least one tryptophan in the amino acid sequence of the new ApoA1 mimetic is substituted with an oxidant resistant amino acid.

The present invention also relates to a method of treating cardiovascular disorders by administering to a subject a pharmaceutical formulation comprising a new ApoA1 mimetic that is capable of promoting cholesterol efflux from lipid loaded cells. The new ApoA1 mimetic includes at least a portion of the amino acid sequence of ApoA1 or a prior mimetic of the ApoA1 that contains at least one tryptophan and is capable of promoting cholesterol efflux from lipid loaded cells. At least one tryptophan in the amino acid sequence of the prior new ApoA1 mimetic is substituted with an oxidant resistant amino acid. The new ApoA1 mimetic can include an amino acid sequence of, for example, a tryptophan containing ApoA1 fragment, native ApoA1, ApoA1 fusion protein, ApoA1 chimeric protein, a truncated ApoA1 protein, or a mimetic of an ApoA1 polypeptide, wherein at least one tryptophan in the amino acid sequence of the new ApoA1 mimetic is substituted with an oxidant resistant amino acid.

The present invention further relates to a method of promoting cholesterol efflux from a lipid loaded cell. The method includes administering to the lipid loaded cell a biologically effective amount of a purified polypeptide. The polypeptide can include an amino acid sequence comprising a cholesterol efflux acceptor portion of SEQ ID NO: 1, wherein X is selected from the group consisting of tryptophan or phenylalanine and at least one X is phenylalanine.

The present invention still further relates to a method of ameliorating one or more symptoms of an inflammatory condition in a subject. The method include administering to the subject a new ApoA1 mimetic that is capable of promoting cholesterol efflux from lipid loaded cells. The new ApoA1 mimetic includes at least a portion of the amino acid sequence of ApoA1 or a prior mimetic of the ApoA1 that contains at least one tryptophan and is capable of promoting cholesterol efflux from lipid loaded cells. At least one tryptophan in the amino acid sequence of the new ApoA1 mimetic is substituted with an oxidant resistant amino acid. The new ApoA1 mimetic can include an amino acid sequence of, for example, a tryptophan containing ApoA1 fragment, native ApoA1, ApoA1 fusion protein, ApoA1 chimeric protein, a truncated ApoA1 protein, or a mimetic of an ApoA1 polypeptide, wherein at least one tryptophan in the amino acid sequence of the new ApoA1 mimetic is substituted with an oxidant resistant amino acid.

Another aspect of the invention relates to a method of mitigating MPO oxidant loss of cholesterol efflux acceptor function of ApoA1, a fragment thereof, or a mimetic thereof that contain at least one tryptophan residue. The method includes substituting at least one tryptophan residue of the ApoA1, fragment thereof, or mimetic of ApoA1 with an oxidant resistant amino acid.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIGS. 5(A-B) illustrate plots showing the effect of tryptophan substitutions to phenylalanine or leucine on rh-ApoA1 function, and the resistance of the phenylalanine substitution to inactivation by MPO. A. Varying concentrations of rh-ApoA1 (closed circles, solid line), rh-ApoA1 4WF (four tryptophans converted to phenylalanine, open circles, dashed line), and rh-ApoA1 4WL (four tryptophans converted to leucine, open squares, dotted line) were assayed for cellular cholesterol acceptor activity as described in FIG. 3. The 4WF variant largely retained this activity, while the 4WL variant lost this activity. Data are means±S.D. of triplicate determinations. B. rh-ApoA1 (filled circles, solid line) and rh-ApoA1 4WF (open circles, dashed line) were subjected to modification by MPO at varying $H_2O_2$:ApoA1 mole ratios. These proteins were then assayed for ABCA1 dependent cellular cholesterol acceptor activity as described in FIG. 3. Data are means±S.D. of triplicate determinations. *, p<0.05; and ** p<0.0001 vs. rh-ApoA1 at the same $H_2O_2$:ApoA1 mole ratio, respectively, by two tailed t-test.

FIGS. 7(A-B) illustrate plots showing that rh-ApoA1 4WF binds lipid as well as rh-ApoA1 and its lipid binding activity is resistant to MPO mediated oxidation. A. Dimyristoyl phosphatidylcholine (DMPC) emulsions (125 µg) were prepared and incubated without addition (solid thick line) or with the addition of 25 µg rh-ApoA1 (solid thin line) or rh-ApoA1 4WF (dotted line). Lipid binding and solubilization was monitored by loss of turbidity by reading absorbance at 325 nm over time at 24° C. (n=3 per condition, mean±S.D.) The 4WF variant yielded similar DMPC clearance compared to wild type rh-ApoA1. B. rh-ApoA1 (filled circles, solid line) and rh-ApoA1 4WF (open circles, dashed line) were subjected to modification by MPO at varying $H_2O_2$:ApoA1 mole ratios. These proteins were then assayed for lipid binding activity by prevention of phospholipase C dependent LDL aggregation. Data are normalized to the lipid binding activity of rh-ApoA1 treated in the absence of $H_2O_2$. Data are means±S.D. of triplicate determinations. *, p<0.05; and **, p<0.001 vs. rh-ApoA1 4WF at the same $H_2O_2$:ApoA1 mole ratio, respectively, by two tailed t-test. The data show that the rh-ApoA1 4WF did not loose its lipid binding activity at a dose of MPO modification that diminished lipid binding activity of wild type rh-ApoA1.

DETAILED DESCRIPTION

Figure 1A:
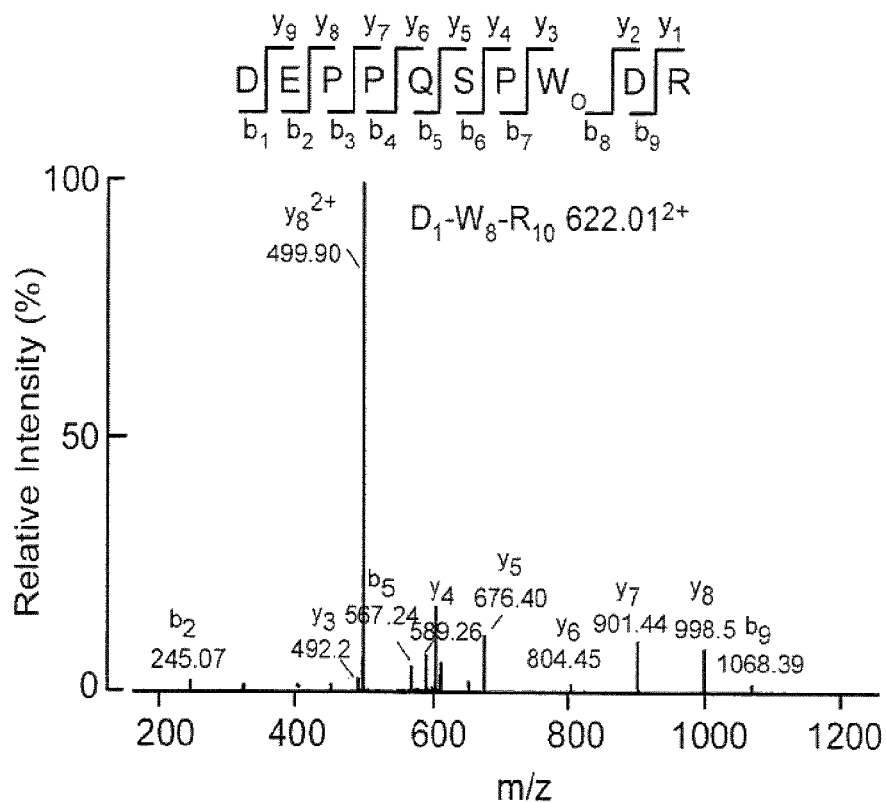
FIG. 1(A-F) illustrate tandem mass spectrometry of protein modifications of ApoA1 isolated from human atheroma tissue. Collision induced dissociation spectra were acquired after direct or in gel tryptic digest of imunnoaffinity purified ApoA1 derived from human atheroma. Doubly charged ions were detected and fragmented in an LC-tandem mass spectrometry experiment. A. Peptide D-R 10 (SEQ ID NO:70) containing monohydroxytryptophan at residue 8. B. Peptide L46-K59 (SEQ ID NO:71) containing monohydroxytryptophan at residue 50. C. Peptide E62-K77 containing monohydroxytryptophan at residue 72 (SEQ ID NO:72). D. Peptide W108-R116 (SEQ ID NO:73) containing monohydroxytryptophan at residue 108 and methionine sulfoxide at residue 112. E. The same peptide as in D, but the tryptophan at residue 108 is converted to dihydroxytryptophan (SEQ ID NO:74). F. Peptide L41-R49 (SEQ ID NO:75) containing methionine sulfoxide as at residue 48.
Figure 1B:
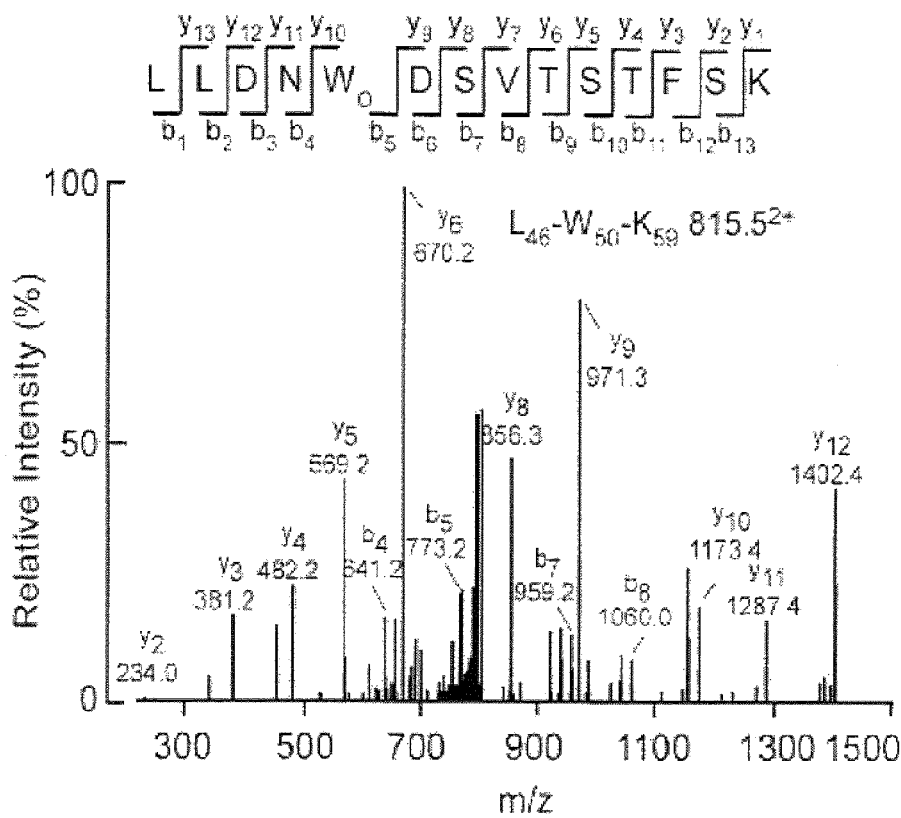
Figure 1C:
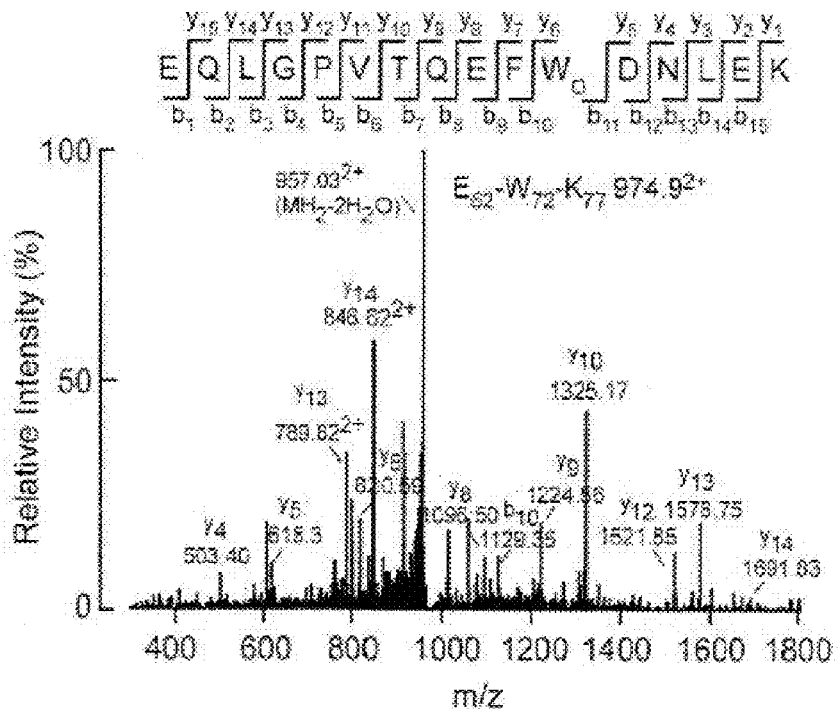

The present invention relates to apolipoprotein A-1 (ApoA1) polypeptide mimetics that are resistant to oxidation when administered to a subject and can increase cellular cholesterol efflux from lipid loaded cells. By "resistant to oxidation" or "oxidant resistant" as used in the specification and the claims, it is meant that the ApoA1 mimetic polypeptide can be at least partially resistant to oxidation that impairs or reduces ApoA1 polypeptide cholesterol accepting and lipid binding activities. The oxidation can be potentially associated with or caused by, for example, oxidation from oxidation pathways including at least one of myeloperoxidase (MPO), a MPO-generated oxidant, a MPO-generated reactive chlorinating species, a MPO/$H_2O_2$/Cl$^-$ system, a HOCl/OCl$^-$, a MPO generated reactive nitrogen species, MPO/$H_2O_2$/NO$_2^-$ system, nitrogen dioxide, peroxynitrite (ONOO$^-$), peroxycarboxynitrite (ONOOCO$_2^-$), and the product formed when ONOO$^-$ acts in the presence of CO$_2$ (or HCO$_3^-$ in buffer).

It was found that tryptophan residues of ApoA1 protein are readily oxidized by, for example, myeloperoxidase (MPO), hypochlorous acid, or potentially other oxidants. Oxidation of the tryptophan residues of ApoA1 leads to its loss of cholesterol accepting and lipid binding activities. Moreover, MPO mediated oxidation of native ApoA1 can potentially inactivate acceptance of cellular cholesterol as part of the reverse cholesterol transport.

ApoA1 oxidant resistant mimetics (or oxidation resistant mimetics) according to the present invention have an amino acid sequence that is substantially similar to the amino acid sequence of ApoA1, ApoA1 fragments, or known mimetics of ApoA1 that contain at least one tryptophan and where at least one tryptophan residues is substituted with oxidant resistant residues, such as an oxidant resistant peptide residue, and for which ApoA1 lipid binding and efflux activities are retained. In one example, the oxidant resistant residue can include an aromatic peptide residue, such as phenylalanine.

By "mimetics of ApoA1" or "prior mimetics or ApoA1" or "known mimetics of ApoA1" as used in the specification and in the claims, it is meant mimetics of ApoA1 that can be identified or derived from any reference and that have ApoA1 behavior. These include mimetics of ApoA1 identified in U.S. and foreign patents and publications. The terms "mimetics of ApoA1" or "prior mimetics or ApoA1" or "known mimetics of ApoA1" are distinguished from the term "ApoA1 mimetics" or "novel ApoA1 mimetics" or "new ApoA1 mimetics" in the specification and claims, which is meant to include the ApoA1 mimetics of the present invention that are resistant to oxidation or oxidant resistant.

The terms "polypeptide", "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. "Aromatic Amino Acid" as used herein, refers to a hydrophobic amino acid with a side chain having at least one aromatic or heteroaromatic ring. The aromatic or heteroaromatic ring may contain one or more substituents such as —O, —SH, —CN, —F, —Br, —I, —NO2, —NO, —NH$_2$, —NHR, —NRR, —C(O)R, —C(O)OH, —C(O)OR, —C(O)NH$_2$, —C(O)NHR, —C(O)NRR and the like where each R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C5-C20) aryl, substituted (C5-C20) aryl, (C6-C26) alkaryl, substituted (C6C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include phenylalanine (F), tyrosine (Y) and tryptophan (W). In one particular example, the oxidation resistant amino acid of the present invention can be phenylalanine.

ApoA1 mimetics that are resistant to oxidation are superior in promoting cholesterol efflux from lipid loaded cells and can be used as therapeutics for treating, ameliorating, and/or preventing coronary vascular disorders (e.g., cardiovascular disease), including both reducing existing plaques and inhibiting developing plaques, atherosclerosis, vascular inflammation, wound healing, and hyperlipidemia. The present invention thus includes methods of treating, preventing, and/or ameliorating coronary vascular disorders, vascular inflammation, wound healing, and/or hyperlipidemia in a subject by administering to the subject therapeutically effective amount of an ApoA1 mimetic in accordance with the present invention.

In an aspect of the invention, the ApoA1 mimetic can include a polypeptide having an amino acid sequence that comprises at least a tryptophan containing and cholesterol efflux acceptor portion of native ApoA1. In one example, the ApoA1 mimetic can have the following amino acid sequence:

```
DEPPQSPXDR VKDLATVYVD VLKDSGRDYV SQFEGSALGK

QLNLKLLDNX DSVTSTFSKL REQLGPVTQE FXDNLEKETE

GLRQEMSKDL EEVKAKVQPY LDDFQKKXQE EMELYRQKVE

PLRAELQEGA RQKLHELQEK LSPLGEEMRD RARAHVDALR

THLAPYSDEL RQRLAARLEA LKENGGARLA EYHAKATEHL

STLSEKAKPA LEDLRQGLLP VLESFKVSFL SALEEYTKKL

NTQ (SEQ ID NO: 1)
``` wherein X is either a tryptophan residue or an oxidant resistant residue (e.g., phenylalanine) and at least one of the four X's is an oxidant resistant residue. In other examples, at least two of the Xs of SEQ ID NO: 1 are an oxidant resistant residue, at least three of the Xs of SEQ ID NO: 1 are oxidant resistant residues, or all four of the Xs are oxidant resistant residues.

The ApoA1 mimetics, besides including tryptophan substituted wild-type or native forms of ApoA 1, can also include tryptophan substituted natural variants of ApoA 1 that are known in the art. For example, Weisgraber et al. has shown that cysteine can be substituted for arginine at position 173 in a mutant ApoA1 termed ApoA1-Milano (Weisgraber et al. (1983) *J. Biol. Chem.* 258: 2508-2513). An ApoA1 mimetic based on ApoA1-Milano can therefore include the amino sequence of SEQ ID NO: 2.

```
DEPPQSPXDR VKDLATVYVD VLKDSGRDYV SQFEGSALGK

QLNLKLLDNX DSVTSTFSKL REQLGPVTQE FXDNLEKETE

GLRQEMSKDL EEVKAKVQPY LDDFQKKXQE EMELYRQKVE

PLRAELQEGA RQKLHELQEK LSPLGEEMRD RARAHVDALR

THLAPYSDEL RQCLAARLEA LKENGGARLA EYHAKATEHL

STLSEKAKPA LEDLRQGLLP VLESFKVSFL SALEEYTKKL

NTQ (SEQ ID NO: 2)
``` wherein X is a tryptophan or an oxidant resistant residue (e.g., phenylalanine) and at least one X is substituted for an oxidant resistant residue.

Another example of ApoA1 mimetic according to the present in invention is based on a known full-length mimetic of human ApoA1 peptide possessing a cysteine residue at position 151 of the mature ApoA1. The ApoA1 mimetic in accordance with this example can include the amino acid sequence of SEQ ID NO: 3.

```
DEPPQSPXDR VKDLATVYVD VLKDSGRDYV SQFEGSALGK

QLNLKLLDNX DSVTSTFSKL REQLGPVTQE FXDNLEKETE

GLRQEMSKDL EEVKAKVQPY LDDFQKKXQE EMELYRQKVE

PLRAELQEGA RQKLHELQEK LSPLGEEMRD CARAHVDALR

THLAPYSDEL RQRLAARLEA LKENGGARLA EYHAKATEHL

STLSEKAKPA LEDLRQGLLP VLESFKVSFL SALEEYTKKL

NTQ (SEQ ID NO: 3)
``` wherein X is a tryptophan or an oxidant resistant residue (e.g., phenylalanine) and at least one X is substituted for an oxidant resistant residue.

Accordingly, the ApoA1 polypeptide mimetics contemplated in the present invention may include modified polypeptides from the ApoA1 forms and variants including, for example, apolipoprotein A-1 (Brewer et al., (1978)), apolipoprotein A-1 Milano (Weisgraber,(1983)), apolipoprotein A-1 Marburg, (Utermann et al., (1982) *J. Biol. Chem.* 257: 501-507), apolipoprotein A-1 Paris (Bielicki and Oda (2002) *Biochemistry* 41, 2089-2096), proapolipoprotein A-1, or any other mutant form of ApoA1 known in the art whether synthetically formed or naturally occurring.

Alternatively, the ApoA1 mimetics of the present invention can include an amphipathic helical peptides that closely mimic the class A amphipathic helix of human or mouse ApoA1 peptide (i.e., mimetics of ApoA1), wherein residues denoted by X can include a tryptophan residue or an oxidant resistant amino acid residue and at least one X is an oxidant resistant residue. The term "an amphipathic helical peptide" refers to a peptide comprising at least one amphipathic helix (amphipathic helical domain). Certain amphipathic helical peptides of this invention can comprise two or more (e.g., 3, 4, 5, etc.) amphipathic helices.

The term "class A amphipathic helix" refers to a protein structure that forms an a-helix producing a segregation of a polar and nonpolar faces with the positively charged residues residing at the polar-nonpolar interface and the negatively charged residues residing at the center of the polar face (see, e.g., Segrest et al. (1990) Proteins: Structure, Function, and Genetics 8: 103-117). Particularly preferred peptides may include greater than about 50% amino acid sequence identity with the polypeptide encoded by the exon encoding a class A amphipathic helix of human or mouse ApoA1. The peptide may be combined with a pharmacologically acceptable excipient (e.g. an excipient suitable for oral administration to a mammal).

In certain embodiments, the ApoA1 mimetic is a fragment or mimetic of ApoA1, which is capable of promoting cholesterol efflux, and comprises one or more of the following amino acid sequences:

| | |
|---|---|
| D-X-L-K-A-F-Y-D-K-V-A-E-K-L-K-E-A-F-, | (SEQ ID NO: 4) |
| D-X-F-K-A-F-Y-D-K-V-A-E-K-L-K-E-A-F-, | (SEQ ID NO: 5) |
| D-X-L-K-A-F-Y-D-K-V-A-E-K-F-K-E-A-F-, | (SEQ ID NO: 6) |
| D-X-F-K-A-F-Y-D-K-V-A-E-K-F-K-E-A-F-, | (SEQ ID NO: 7) |
| D-X-L-K-A-F-Y-D-K-V-F-E-K-F-K-E-F-F-, | (SEQ ID NO: 8) |
| D-X-L-K-A-F-Y-D-K-F-F-E-K-F-K-E-F-F-, | (SEQ ID NO: 9) |
| D-X-F-K-A-F-Y-D-K-F-F-E K-F-K-E-F-F-, | (SEQ ID NO: 10) |
| D-X-L-K-A-F-Y-D-K-V-F-E-K-F-K-E-A-F-, | (SEQ ID NO: 11) |

-continued

| | |
|---|---|
| D-X-L-K-A-F-Y-D-K-V-F-E-K-F-K-E-A-F-, | (SEQ ID NO: 12) |
| D-X-L-K-A-F-Y-D-K-V-F-E-K-L-K-E-F-F-, | (SEQ ID NO: 13) |
| D-X-L-K-A-F-Y-D-K-V-A-E-K-F-K-E-F-F-, | (SEQ ID NO: 14) |
| D-X-L-K-A-F-Y-D-K-V-F-E-K-F-K-E-F-F-, | (SEQ ID NO: 15) |
| E-X-L-K-L-F-Y-E-K-V-L-E-K-F-K-E-A-F-, | (SEQ ID NO: 16) |
| E-X-L-K-A-F-Y-D-K-V-A-E-K-F-K-E-A-F-, | (SEQ ID NO: 17) |
| E-X-L-K-A-F-Y-D-K-V-A-E-K-L-K-E-F-F-, | (SEQ ID NO: 18) |
| E-X-L-K-A-F-Y-D-K-V-F-E-K-F-K-E-A-F-, | (SEQ ID NO: 19) |
| E-X-L-K-A-F-Y-D-K-V-F-E-K-L-K-E-F-F-, | (SEQ ID NO: 20) |
| E-X-L-K-A-F-Y-D-K-V-A-E-K-F-K-E-F-F-, | (SEQ ID NO: 21) |
| E-X-L K-A-F-Y-D-K-V-F-E-K-F-K-E-F-F-, | (SEQ ID NO: 22) |
| D-X-L-K-A-L-Y-D-K-V-A-E-K-L-K-E-A-L-, | (SEQ ID NO: 23) |
| D-X-F-K-A-F-Y-E-K-V-A-E-K-L-K-E-F-F-, | (SEQ ID NO: 24) |
| D-X-F-K-A-F-Y-E-K-F-F-E-K-F-K-E-F-F-, | (SEQ ID NO: 25) |
| E-X-L-K-A-L-Y-E-K-V-A-E-K-L-K-E-A-L-, | (SEQ ID NO: 26) |
| E-X-L-K-A-F-Y-E-K-V-A-E-K-L-K-E-A-F-, | (SEQ ID NO: 27) |
| E-X-F-K-A-F-Y-E-K-V-A-E-K-L-K-E-F-F-, | (SEQ ID NO: 28) |
| E-X-L-K-A-F-Y-E-K-V-F-E-K-F-K-E-F-F-, | (SEQ ID NO: 29) |
| E-X-L-K-A-F-Y-E-K-F-F-E-K-F-K-E-F-F-, | (SEQ ID NO: 30) |
| E-X-F-K-A-F-Y-E-K-F-F-E-K-F-K-E-F-F-, | (SEQ ID NO: 31) |
| D-F-L-K-A-X-Y-D-K-V-A-E-K-L-K-E-A-X-, | (SEQ ID NO: 32) |
| E-F-L-K-A X-Y-E-K-V-A-E-K-L-K-E-A-X-, | (SEQ ID NO: 33) |
| D-F-X-K-A-X-Y-D-K-V-A-E-K-L-K-E-X-X-, | (SEQ ID NO: 34) |
| E-F-X-K-A-X-Y-E-K-V-A-E-K-L-K-E-X-X-, | (SEQ ID NO: 35) |
| D-K-L-K-A-F-Y-D-K-V-F-E-X-A-K-E-A-F-, | (SEQ ID NO: 36) |
| D-K-X-K-A-V-Y-D-K-F-A-E-A-F-K-E-F-L-, | (SEQ ID NO: 37) |
| E-K-L-K-A-F-Y-E-K-V-F-E-X-A-K-E-A-F-, | (SEQ ID NO: 38) |
| E-K-X-K-A-V-Y-E-K-F-A-E-A-F-K-E-F-L-, | (SEQ ID NO: 39) |
| D-X-L-K-A-F-V-D-K-F-A-E-K-F-K-E-A-Y-, | (SEQ ID NO: 40) |
| E-K-X-K-A-V-Y-E-K-F-A-E-A-F-K-E-F-L-, | (SEQ ID NO: 41) |
| D-X-L-K-A-F-V-Y-D-K-V-F-K-L-K-E-F-F-, | (SEQ ID NO: 42) |
| E-X-L-K-A-F-V-Y-E-K-V-F-K-L-K-E-F-F-, | (SEQ ID NO: 43) |
| D-X-L-R-A-F-Y-D-K-V-A-E-K-L-K-E-A-F-, | (SEQ ID NO: 44) |
| E-X-L-R-A-F-Y-E-K-V-A-E-K-L-K-E-A-F-, | (SEQ ID NO: 45) |
| D-X-L-K-A-F-Y-D-R-V-A-E-K-L-K-E-A-F-, | (SEQ ID NO: 46) |
| E-X-L-K-A-F-Y-E-R-V-A-E-K-L-K-E-A-F-, | (SEQ ID NO: 47) |
| D-X-L-K-A-F-Y-D-K-V-A-E-R-L-K-E-A-F-, | (SEQ ID NO: 48) |
| E-X-L-K-A-F-Y-E-K-V-A-E-R-L-K-E-A-F-, | (SEQ ID NO: 49) |
| D-X-L-K-A-F-Y-D-K-V-A-E-K-L-R-E-A-F-, | (SEQ ID NO: 50) |
| E-X-L-K-A-F-Y-E-K-V-A-E-K-L-R-E-A-F-, | (SEQ ID NO: 51) |
| D-X-L-K-A-F-Y-D-R-V-A-E-R-L-K-E-A-F-, | (SEQ ID NO: 52) |

-continued

E-X-L-K-A-F-Y-E-R-V-A-E-R-L-K-E-A-F-, (SEQ ID NO: 53)

D-X-L-R-A-F-Y-D-K-V-A-E-K-L-R-E-A-F-, (SEQ ID NO: 54)

E-X-L-R-A-F-Y-E-K-V-A-E-K-L-R-E-A-F-, (SEQ ID NO: 55)

D-X-L-R-A-F-Y-D-R-V-A-E-K-L-K-E-A-F-, (SEQ ID NO: 56)

X-L-R-A-F-Y-E-R-V-A-E-K-L-K-E-A-F-, (SEQ ID NO: 57)

D-X-L-K-A-F-Y-D-K-V-A-E-R-L-R-E-A-F-, (SEQ ID NO: 58)

E-X-L-K-A-F-Y-E-K-V-A-E-R-L-R-E-A-F-, (SEQ ID NO: 59)

D-X-L-R-A-F-Y-D-K-V-A-E-R-L-K-E-A-F-, (SEQ ID NO: 60)

E-X-L-R-A-F-Y-E-K-V-A-E-R-L-K-E-A-F-, (SEQ ID NO: 61)

D-X-L-K-A-F-Y-D-K-V-A-E-K-L-K-E-A-F-P-D-X-L-K-A-F-Y-D-K-V-A-E-K-L-K-E-A-F, (SEQ ID NO: 62)

D-X-L-K-A-F-Y-D-K-V-A-E-K-L-K-E-F-P-D-X-L-K-A-F-Y-D-K-V-A-E-K-L-K-E-F-F, (SEQ ID NO: 63)

D-X-F-K-A-F-Y-D-K-V-A-E-K-L-K-E-A-F-P-D-X-F-K-A-F-Y-D-K-V-A-E-K-L-K-E-A-F, (SEQ ID NO: 64)

D-K-L-K-A-F-Y-D-K-V-F-E-X-A-K-E-A-F-P-D-K-L-K-A-F-Y-D-K-V-F-E-X-L-K-E-A-F, (SEQ ID NO: 65)

D-K-X-K-A-V-Y-D-K-F-A-E-A-F-K-E-F-L-P-D-K-X-K-A-V-Y-D-K-F-A-E-A-F-K-E-F-L, (SEQ ID NO: 66)

D-X-F-K-A-F-Y-D-K-V-A-E-F-K-E-A-F-P-D-X-F-K-A-F-Y-D-K-V-A-E-K-F-K-E-A-F, (SEQ ID NO: 67)

D-X-L-K-A-F-V-Y-D-K-V-F-K-L-K-E-F-F-P-D-X-L-K-A-F-V-Y-D-K-V-F-K-L-K-E-F-F, (SEQ ID NO: 68)
and D-X-L-K-A-F-Y-D-K-F-A-E-K-F-K-E-F-F-P-D-X-L-K-A-F-Y-D-K-F-A-E-K-F-K-E-F-F; (SEQ ID NO: 69)

wherein X is a tryptophan or an oxidant resistant residue (e.g., phenylalanine) and at least one X in each sequence is substituted for an oxidant resistant residue.

The above referenced sequences (SEQ ID NO:4-SEQ ID NO:69) are described in U.S. Pat. No. 7,144,862 B2 to Fogelman et al. (hereinafter the '862 patent), which is incorporated by reference in its entirety. The '862 patent is directed towards peptides used to ameliorate one or more symptoms of atherosclerosis. The peptides described in the '862 patent include a tryptophan residue at each residue designated herein with an X. The synthetic peptides of the '862 patent were designed to mimic the class A amphipathic helical motif (Segrest et al. (1990) *Proteins: Structure, Function and Genetics* 8:103-117)) and are able to associates with phospholipids and exhibit many biological properties similar to human ApoA1.

It is also noted that this list of ApoA1 mimetic peptides is not fully inclusive. Truncations of the above sequences, multimeric combinations (e.g., ranging from dimers to trimers, tetramers, 5 mers, 8 mers, or 10 mers) of the above sequences, conservative substitutions of the above sequences, and/or the above sequences comprising amino acid analogs are also contemplated using the teachings provided within.

It will be appreciated that biologically functional equivalents, or even improvements, of the ApoA1 mimetic polypeptides, can be made, generally using ApoA1 as a starting point. Modifications and changes may be made in the structure of such a protein and still obtain a molecule having like or otherwise desirable characteristics. For example, certain amino acids may be substituted for other amino acids in the protein structure without appreciable loss of cholesterol efflux acceptor activity.

It should be contemplated as well that one skilled in the art can further modify the ApoA1 amino acid sequences of the present invention by substitution, deletion or addition of at least one amino acid, and that these further modifications create biologically functional equivalents to the oxidant resistant ApoA1 polypeptides. These substitutions do not substantially inhibit modified ApoA1's ability to promote cholesterol efflux from loaded lipid cells. As used herein, "substantially inhibit" or "inhibition" includes any measurable reproducible reduction in the ability of a modified ApoA1 polypeptide to promote cholesterol efflux from loaded lipid cells.

It is also well understood by the skilled artisan that, inherent in the definition of a "biologically functional equivalent" protein or polypeptide, is the concept that there is a limit to the number of changes that may be made within a defined portion of the molecule and still result in a molecule with an acceptable level of equivalent biological activity. Biologically functional equivalent proteins and peptides are thus defined herein as those proteins and peptides in which certain, not most or all, of the amino acids may be substituted. Of course, a plurality of distinct proteins/peptides with different substitutions may easily be made and used in accordance with the invention.

Amino acid substitutions ate generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size. Therefore, based upon these considerations, arginine, lysine and histidine; alanine, glycine and serine are defined herein as biologically functional equivalents.

Following the procedures noted in the published application by Alton et al. (WO83/04053), one can readily design and manufacture genes coding for microbial expression of polypeptides having primary conformations which differ from that herein specified in terms of the identity or location of one or more residues (e.g., substitutions, terminal and intermediate additions and deletions). Alternately, modifications of cDNA and genomic genes may be readily accomplished by well-known site-directed mutagenesis techniques and employed to generate analogs and derivatives of ApoA1. Such products would share at least one of the biological properties of oxidant resistant modified ApoA1 but may differ in others.

In accordance with another aspect of the present invention, the ApoA1 mimetic polypeptides can be fragments of full-length human ApoA1 peptides. The ApoA1 fragments of the present invention are biologically functional equivalents to the ApoA1 polypeptides described above in at least one aspect including but not limited to cholesterol efflux promotion and ameliorating one or more symptoms of an inflammatory condition. The ApoA1 fragments can consist of about 5 to about 50 amino acids and include at least one tryptophan residue, wherein the tryptophan residue is substituted with an oxidant resistant amino acid.

It will be appreciated that as with the ApoA1 mimetic polypeptide, modifications and changes may be made in the structure and amino sequence of the ApoA1 fragments and still obtain a molecule having like or otherwise desirable functional characteristics. For example, certain amino acids may be substituted for other amino acids in a protein structure without appreciable loss of cholesterol efflux promotion.

The ApoA1 mimetic polypeptides of the present invention can also include a protecting group coupled to the amino-terminus and/or the carboxyl-terminus of the polypeptides. The term "protecting group" refers to a chemical group that, when attached to a functional group in an amino acid (e.g., a side chain, an alpha amino group, an alpha carboxyl group, etc.) blocks or masks the properties of that functional group. Examples of amino-terminal protecting groups include, but are not limited to acetyl, or amino groups. In such an embodiment, the first one to four amino acid residues at the N-terminus and/or C-terminus of the polypeptides described herein can be substituted with one or more amino acid residues, or one or more peptide segments, that are known to confer stability to regions of α-helical secondary structure ("end-cap" or "protecting groups" residues or segments). Such end-cap residues and segments are well-known in the art (see, e.g., Richardson and Richardson, 1988, Science 240: 1648-1652; Harper et al., 1993, Biochemistry 32(30):7605-7609; Dasgupta and Bell, 1993, Int. J. Peptide Protein Res. 41:499-511; Scale et al., 1994, Protein Science 3:1741-1745; Doig et al., 1994, Biochemistry 33:3396-3403; Zhou et al., 1994, Proteins 18:1-7; Doig and Baldwin, 1995, Protein Science 4:1325-1336; Odaert et al., 1995, Biochemistry 34:12820-12829; Petrukhov et al., 1996, Biochemistry 35:387-397; Doig et al., 1997, Protein Science 6:147-155). Alternatively, the first one to four N-terminal and/or C-terminal amino acid residues of the polypeptides described herein can be replaced with peptidomimetic moieties that mimic the structure and/or properties of end-cap residues or segments. Examples of end-cap mimetics are well-known in the art, and are described, for example, in Richardson and Richardson, 1988, Science 240:1648-1652; Harper et al., 1993, Biochemistry 32(30):7605-7609; Dasgupta and Bell, 1993, Int. J. Peptide Protein Res. 41:499511; Seale et al., 1994, Protein Science 3:1741-1745; Doig et al., 1994, Biochemistry 33:3396-3403; Zhou et al., 1994, Proteins 18:1-7; Doig and Baldwin, 1995, Protein Science 4:1325-1336; Odaert et al., 1995, Biochemistry 34:1282012829; Petrukhov et al., 1996, Biochemistry 35:387-397; Doig et al., 1997, Protein Science 6:147-155).

The ApoA1 mimetic polypeptides of the present invention may be purified and isolated. The term "purified and isolated" herein means substantially free of unwanted substances so that the present polypeptides of modified ApoA1 mimetics or fragments thereof are useful for promoting cholesterol efflux from lipid loaded cells. For example, one may have a modified recombinant human ApoA1 mimetic polypeptide substantially free of other human proteins or pathological agents. These polypeptides are also characterized by being a product of mammalian cells, or the product of chemical synthetic procedures or of prokaryotic or eukaryotic host expression (e.g., by bacterial, yeast, higher plant, insect and mammalian cells in culture) of exogenous DNA sequences obtained by genomic or cDNA cloning or by gene synthesis. The products of expression in typical yeast (e.g., *Saccharomyces cerevisiae*) or prokaryote (e.g, *E. coli*) host cells are free of association with any mammalian proteins. The products of expression in vertebrate (e.g., non-human mammalian (e.g., COS or CHO) and avian) cells are free of association with any human proteins. Depending upon the host employed, and other factors, polypeptides of the invention may be glycosylated with mammalian or other eucaryotic carbohydrates or may be non-glycosylated. Polypeptides of the invention may also include an initial methionine amino acid residue (at position-1 with respect to the first amino acid residue of the polypeptide).

The peptides of the invention can be purified by art-known techniques such as reverse phase chromatography high performance liquid chromatography, ion exchange chromatography, gel electrophoresis, affinity chromatography and the like. The actual conditions used to purify a particular peptide will depend, in part, on the synthesis strategy and on factors, such as net charge, hydrophobicity, hydrophilicity, etc., and will be apparent to those having skill in the art. Multimeric branched peptides can be purified, e.g., by ion exchange or size exclusion chromatography.

For affinity chromatography purification, any antibody which specifically binds the peptide may be used. For the production of antibodies, various host animals, including but not limited to rabbits, mice, rats, etc., may be immunized by injection with a peptide. The peptide may be attached to a suitable carrier, such as BSA, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Kohler and Milstein, 1975, Nature 256:495497, or Kaprowski, U.S. Pat. No. 4,376,110, which is incorporated by reference herein; the human B-cell hybridoma technique) (Kosbor et al., 1983, Immunology Today 4:72; Cote et al., 1983, Proc. Natl. Acad. Sci. U.S.A. 80:2026-2030); and the EBV-hybridoma technique (Cole et al., 1985, Monoclonal Antibodies and Cancer Therapy, Alan R. Liss, Inc., pp. 77-96 (1985)). In addition, techniques developed for the production of "chimeric antibodies" (Morrison et al., 1984, Proc. Natl. Acad. Sci. U.S.A. 81:68516855; Neuberger et al., 1984, Nature 312:604-608; Takeda et al., 1985, Nature 314:452-454, Boss, U.S. Pat. No. 4,816,397; Cabilly, U.S. Pat. No. 4,816,567; which are incorporated by reference herein) by splicing the genes from a mouse antibody molecule of appropriate antigen specificity together with genes from a human antibody molecule of appropriate biological activity can be used. Or "humanized" antibodies can be prepared (see, e.g., Queen, U.S. Pat. No. 5,585,089 which is incorporated by reference herein). Alternatively, techniques described for the production of single chain antibodies (U.S. Pat. No. 4,946,778) can be adapted to produce peptide-specific single chain antibodies.

Antibody fragments that contain deletions of specific binding sites may be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, Protein Purification: Principles and Practice, Springer-Verlag New York, Inc., NY, Livingstone, 1974, Methods In Enzymology: Immunoaffinity Chromatography of Proteins 34; 723-731.

The present invention also contemplates ApoA1 mimetic polypeptides including a polyhistidine-tag. A polyhistidine-tag is an amino acid motif in proteins that consists of at least six histidine (His) residues, often at the N- or C-terminus of the protein. It is also known as hexa histidine-tag, 6×His-tag, and by the trademarked name His-tag® (EMD Biosciences). Polyhistidine-tags can be used for affinity purification of polyhistidine-tagged recombinant proteins that are expressed in *Escherichia coli* or other prokaryotic expression systems. The bacterial cells are harvested by centrifuigation and the resulting cell pellet can be lysed by physical means or with detergents or enzymes, such as lysozyme. The raw lysate contains at this stage the recombinant protein among several other proteins derived from the bacteria and are incubated with affinity media such as NTA-agarose, HisPur resin or Talon resin. These affinity media contain bound metal ions, either nickel or cobalt to which the polyhistidine-tag binds with micromolar affinity. The resin is then washed with phosphate buffer to remove proteins that do not specifically interact with the cobalt or nickel ion. The washing efficiency can be improved by the addition of 20 mM imidazole and proteins are then usually eluted with 150-300 mM imidazole, but higher concentrations are used as well. The purity and amount of protein can be assessed by SDS-PAGE and western blotting.

Affinity purification using a polyhistidine-tag usually results in relatively pure protein when the recombinant protein is expressed in a prokaryotic host organism. In special cases or for special purposes like the purification of protein complexes to study modified ApoA1 polypeptide interactions, purification from higher organisms such as yeast, insect cell or other eukaryotes may require a tandem affinity purification using two tags to yield higher purity. Alternatively, single-step purification using immobilized cobalt ions rather than nickel ions generally yields a substantial increase in purity and requires lower imidazole concentrations for elution of the his-tagged protein.

Another aspect of the invention relates to nucleic acids coding for the modified ApoA1 mimetic polypeptides as defined above. The nucleic acids of the present invention can be a deoxyribonucleic acid (DNA) or a ribonucleic acid (RNA). Among DNAs, an ApoA1 complementary DNA (cDNA) (e.g. Breslow et al. (1982) *Proc. Nat. Acad. Sci.* 79: 6861-6865, who isolated and characterized cDNA clones for human ApoA1), a genomic DNA (gDNA), a hybrid sequence or a synthetic or semi-synthetic sequence may be used. The nucleic acid may, in addition, be one which is chemically modified, for example for the purpose of increasing its resistance to nucleases, its cell penetration or cell targeting, its therapeutic efficacy, and the like. These nucleic acids may be of human, animal, vegetable, bacterial, viral, synthetic, and the like, origin. They may be obtained by any technique known to a person skilled in the art, and in particular by the screening of libraries, by chemical synthesis or alternatively by mixed methods including chemical or enzymatic modification of sequences obtained by the screening of libraries.

A further aspect of the present invention relates to nucleic acid sequences useful in facilitating expression in prokaryotic or eukaryotic host cells of polypeptides or proteins comprising at least a portion of the ApoA1 mimetic. For the production of recombinant ApoA1 mimetics according to the invention, the nucleic acids can be incorporated in a viral or plasmid vector, which can be an autonomously replicating or integrative vector. This vector is then used to transfect or infect a chosen cell population. The transfected or infected cells thereby obtained are then cultured under conditions permitting the expression of the nucleic acid, and the recombinant ApoA1 mimetic according to the invention is isolated. The cell hosts which can be used for the production of the variants of the invention by recombinant means are either eukaryotic or prokaryotic hosts. Examples of eukaryotic hosts include animal cells, yeasts, or fungi. In particular, as regard to yeasts, yeasts of the genus *Saccharomyces, Kluyveromyces, Pichia, Schwanniomyces* or *Hansenula* can be used. As regards to animal cells, COS, CHO, C127, NIH-3T3, and the like, cells, can be used. Among fungi, *Aspergillus* ssp. or *Trichoderma* ssp. can be used. As regards to prokaryotic hosts, for example, one may use the following bacteria: *E. coli, Bacillus or Streptomyces*. The variant thus isolated may then be packaged with a view to its therapeutic use.

Therefore, in accordance with another embodiment of the present invention, nucleic acids are provided coding for a polypeptide having a modified amino acid sequence of ApoA1 mimetics or fragment thereof that is capable of promoting cholesterol efflux from lipid loaded cells. The amino acid sequence is modified by substituting at least one tryptophan of the amino acid sequence for an oxidant resistant amino acid.

If the peptide is composed entirely of gene-encoded amino acids, or a portion of it is so composed, the polypeptide or the relevant portion may also be synthesized using conventional recombinant genetic engineering techniques. For recombinant production, a polynucleotide sequence encoding the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell, which will express the peptide. Depending on the expression system used, the expressed peptide is then isolated by procedures well-established in the art. Methods for recombinant protein and peptide production are well known in the art (see, e.g., Sambrook et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y. each of which is incorporated by reference herein in its entirety.)

To increase efficiency of production, the polynucleotide can be designed to encode multiple units of the peptide separated by enzymatic cleavage sites-either homopolymers (repeating peptide units) or heteropolymers (different peptides strung together) can be engineered in this way. The resulting polypeptide can be cleaved (e.g., by treatment with the appropriate enzyme) in order to recover the peptide units. This can increase the yield of peptides driven by a single promoter. In one example, a polycistronic polynucleotide can be designed so that a single mRNA is transcribed, which encodes multiple peptides (i.e., homopolymers or heteropolymers) each coding region operatively linked to a cap-independent translation control sequence; e.g., an internal ribosome entry site (IRES). When used in appropriate viral expression systems, the translation of each peptide encoded by the mRNA is directed internally in the transcript; e.g., by the IRES. Thus, the polycistronic construct directs the transcription of a single, large polycistronic mRNA which, in turn, directs the translation of multiple, individual peptides. This approach eliminates the production and enzymatic processing of polyproteins and may significantly increase yield of peptide driven by a single promoter.

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of transcription and translation elements, including constitutive and inducible promoters, may be used in the expression vector. For example, when cloning in bacterial systems, inducible promoters, such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning, in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups, such as peptides (e.g., for targeting host cell receptors in vivo), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. USA 84:648-652; PCT Publication No. WO 88/09810, published Dec. 15, 1988), hybridization-triggered cleavage agents. (See, e.g., Krol et al. (1988) BioTechniques 6:958-976) or intercalating agents. (See, e.g, Zon (1988) Pharm. Res. 5:539-549). To this end, the oligonucleotides may be conjugated to another molecule, e.g., a peptide, hybridization triggered cross-linking agent, transport agent, hybridization-triggered cleavage agent, etc.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. (USA) 81:3655-3659). Alternatively, the vaccinia 7.5 K promoter may be used, (see, e.g., Mackett et al., 1982, Proc. Natl. Acad. Sci. (USA) 79:7415-7419; Mackett et al., 1984, J. Virol. 49:857-864; Panicali et al., 1982, Proc. Natl. Acad. Sci. 79:4927-4931).

Other expression systems for producing the polypeptides of the invention will be apparent to those having skill in the art. According to another aspect of the present invention, the DNA sequences described herein, which encode modified ApoA1 polypeptides are valuable for the information that they provide concerning the amino acid sequence of the mammalian protein which have heretofore been unavailable. Put another way, DNA sequences provided by the invention are useful in generating new and useful viral and circular plasmid DNA vectors, new and useful transformed and transfected prokaryotic and eukaryotic host cells (including bacterial and yeast cells and mammalian cells grown in culture), and new and useful methods for cultured growth of such host cells capable of expression of modified oxidant resistant ApoA1 polypeptides and its related products.

Alternatively, one may use no vector so as to facilitate relatively stable presence in the host. For example, homologous recombination may facilitate integration into a host genome. The nucleic acid may be placed within a pharmaceutically acceptable carrier to facilitate cellular uptake, such as a lipid solution carrier (e.g., a charged lipid), a liposome, or polypeptide carrier (e.g., polylysine. A review article on gene therapy is Verma, *Scientific American*, November 1990, pages 68-84 which is herein incorporated by reference.

The desired nucleic acid may be first placed within a cell, and the cell may be administered to a patient (such as a transplanted tissue) or the desired nucleic acid may be administered directly to the patient for uptake in vivo. The cells to be transferred to the recipient may be cultured using one or more factors affecting the growth or proliferation of such cells, as for example, SCF.

Nucleic acid molecules encoding a modified oxidant resistant ApoA1 mimetic conjugate, such as a fusion protein, may also be used in the invention. Such nucleic acids can be made by preparing a construct (e.g., an expression vector) that expresses an ApoA1 mimetic fusion protein when introduced into a suitable host. For example, such a construct can be made by ligating a first polynucleotide encoding a modified oxidant resistant ApoA1 mimetic protein capable of promoting cholesterol efflux from lipid loaded cells, fused in frame with a second polynucleotide encoding another protein such that expression of the construct in a suitable expression system yields a fusion protein.

ApoA1 mimetic fusion proteins can be readily prepared using molecular biological techniques. Any fusion protein may be designed and made using any of the therapeutic agents disclosed herein and those known in the art. The fusion protein technology is readily adapted to prepare fusion proteins in which the two portions are joined by a selectively cleavable peptide sequence. The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizer.

The preparation of such a fusion protein generally entails the preparation of a first and second DNA coding region and the functional ligation or joining of such regions, in frame, to prepare a single coding region that encodes the desired fusion protein. It is not generally believed to be particularly relevant which portion of the construct is prepared as the N-terminal region or as the C-terminal region.

The present invention also relates to pharmaceutical compositions and/or formulations and the use of such compositions in the treatment of hyperlipidemia, hypercholesterolemia, coronary heart disease, and atherosclerosis. The pharmaceutical compositions of the invention can include the ApoA1 mimetic polypeptide or fragment thereof as the active ingredient and a pharmaceutically acceptable excipient suitable for administration and delivery. in vivo. The pharmaceutical compositions will generally comprise an effective amount of modified ApoA1 polypeptides or fragments thereof, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

Examples of carriers include solvents and dispersion media containing, for example, water, ethanol, polyol (for example, glycerol, propylene glycol, and liquid polyethylene glycol, and the like), mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

The present invention contemplates the administration of the described pharmaceutical compositions by various routes. Pharmaceutical compositions comprising ApoA1 mimetic polypeptides or fragments thereof of the invention may be administered by any route that ensures bioavailability in the circulation. These routes can include, but are by no means limited to oral administration, nasal administration, rectal administration, intraperitoneal injection, intravascular injection, subcutaneous injection, transcutaneous administration, inhalation administration, and intramuscular injection.

Injectable preparations include sterile suspensions, solutions or emulsions of the active ingredient in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a vehicle, including but not limited to sterile pyrogen free water, buffer, dextrose solution, etc., before use. To this end, the ApoA1 mimetic polypeptides of the present invention may be lyophilized, or the co-lyophilized peptide-lipid complex may be prepared. The stored preparations can be supplied in unit dosage forms and reconstituted prior to use in vivo.

For prolonged delivery, the active ingredient can be formulated as a depot preparation, for administration by implantation; e.g., subcutaneous, intradermal, or intramuscular injection. Thus, for example, the active ingredient may be formulated with polymeric or hydrophobic materials (e.g., as an emulsion in an acceptable oil) or ion exchange resins, or as sparingly soluble derivatives; e.g., as a sparingly soluble salt form of the modified ApoA1 polypeptides or fragments thereof.

Alternatively, transdermal delivery systems manufactured as an adhesive disc or patch which slowly releases the active ingredient for percutaneous absorption may be used. To this end, permeation enhancers may be used to facilitate transdermal penetration of the active ingredient. A particular benefit may be achieved by incorporating the modified ApoA1 polypeptides or fragments thereof of the invention or the peptide-lipid complex into a nitroglycerin patch for use in patients with ischemic heart disease and hypercholesterolemia.

For oral administration, the pharmaceutical compositions may take the form of, for example, tablets or capsules prepared by conventional means with pharmaceutically acceptable excipients, such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration, the compositions may take the form of tablets or lozenges formulated in conventional manner. For rectal and vaginal routes of administration, the active ingredient may be formulated as solutions (for retention enemas) suppositories or ointments.

For administration by inhalation, the active ingredient can be conveniently delivered in the form of an aerosol spray presentation from pressurized packs or a nebulizer, with the use of a propellant, e.g., dichlorodifluoromethane, trichlorofluoromethane, dichlorotetrafluoroethane, carbon dioxide or other gas. In the case of a pressurized aerosol, the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the modified ApoA1 polypeptides or fragments thereof should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Pharmaceutical "slow release" capsules or "sustained release" compositions or preparations may be used and are generally applicable. Slow release formulations are generally designed to give a constant drug level over an extended period and may be used to deliver ApoA1 mimetic polypeptides or fragments thereof in accordance with the present invention.

In certain embodiments, liposomes and/or nanoparticles may also be employed with the ApoA1 mimetic polypeptides or fragments thereof. The formation and use of liposomes is generally known to those of skill in the art, as summarized below. Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 containing an aqueous solution in the core. ApoA1 mimetic polypeptides of fragments thereof can also formulated be into phospholipid discs of between 8 and 20 nm, through spontaneous reaction with phospholipid liposomes, or through the cholate dialysis procedure.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made.

Additional pharmacologically active agents may be delivered along with the primary active agents, e.g., the peptides of this invention. Therapies may include, but are not limited to simultaneous or sequential administration of the drugs involved. In one embodiment, such agents include, but are not limited to agents that reduce the risk of atherosclerotic events and/or complications thereof. Such agents include, but are not limited to beta blockers, beta blockers and thiazide diuretic combinations, statins, aspirin, ace inhibitors, ace receptor inhibitors (ARBs), and the like.

Examples of beta blockers include, but are not limited to cardioselective (selective beta 1 blockers), e.g., acebutolol (Sectral), atenolol (Tenormin), betaxolol (Kerlone), bisoprolol (Zebeta), metoprolol (Lopressor), and the like. Examples of non-selective blockers (block beta 1 and beta 2 equally) include, but are not limited to carteolol (Cartrol), nadolol (Corgard), penbutolol (Levatol), pindolol (Visken), propranolol (Inderal), timolol (Blockadren), labetalol (Normodyne, Trandate), and the like.

Examples of beta blocker thiazide diuretic combinations include, but are not limited to Lopressor HCT, ZIAC, Tenoretic, Corzide, Timolide, Inderal LA 40/25, Inderide, Normozide, and the like.

Examples statins include, but are not limited to pravastatin (Pravachol/Bristol-Myers Squibb), simvastatin (Zocor/Merck), lovastatin (Mevacor/Merck), Lipitor (Pfizer), and the like.

Examples of ace inhibitors include, but are not limited to captopril (e.g. Capoten by Squibb), benazepril (e.g., Lotensin by Novartis), enalapril (e.g., Vasotec by Merck), fosinopril (e.g., Monopril by Bristol-Myers), lisinopril (e.g. Prinivil by Merck or Zestril by Astra-Zeneca), quinapril (e.g., Accupril by Parke-Davis), ramipril (e.g., Altace by Hoechst Marion Roussel, King Pharmaceuticals), imidapril, perindopril erbumine (e.g., Aceon by Rhone-Polenc Rorer), trandolapril (e.g., Mavik by Knoll Pharmaceutical), and the like. Suitable ARBS (Ace Receptor Blockers) include but are not limited to losartan (e.g. Cozaar by Merck), irbesartan (e.g., Avapro by Sanofi), candesartan (e.g., Atacand by Astra Merck), valsartan (e.g., Diovan by Novartis), and the like.

Another aspect of the invention relates to a method of treating cardiovascular disorders. "Cardiovascular disorder" as used herein refers to the class of disorders that involve the heart or blood vessels (arteries and veins). "Cardiovascular disorder" further refers to any disease that affects the cardiovascular system, it can be used to refer to those related to atherosclerosis (arterial disease). Cardiovascular disorders can include, but are not limited to Aneurysms, Angina, Arrhythmia, Atherosclerosis, Cardiomyopathy, Cerebrovascular Disease, Congenital Heart Disease, Congestive Heart Failure, Myocarditis, Valve Disease, Coronary Artery Disease, Dilated cardiomyopathy, Diastolic Dysfunction, Endocarditis, High Blood Pressure (Hypertension), Hypertrophic Cardiomyopathy, Mitral valve prolapse, Heart Attack, Vascular Stenosis and Venous Thromboembolism.

"Arteriosclerosis" as used herein refers to any hardening (and loss of elasticity) of medium or large arteries (in Greek, "Arterio" meaning artery and "sclerosis" meaning hardening), arteriolosclerosis is atherosclerosis mainly affecting the arterioles (small arteries). "Atherosclerosis" as used herein refers to a hardening of an artery specifically due to an atheromatous plaque. Therefore, atherosclerosis is a form of arteriosclerosis. Atherosclerosis is a chronic inflammatory response in the walls of arteries, in large part due to the deposition of lipoproteins (plasma proteins that carry cholesterol and triglycerides). It is commonly referred to as a "hardening" or "furring" of the arteries. It is caused by the formation of multiple plaques within the arteries.

The method described herein includes the step of administering to a subject a therapeutically effective or biologically effective amount of a pharmaceutical composition including an ApoA1 mimetic or fragment thereof that is capable of promoting cholesterol efflux from lipid loaded cells. The ApoA1 mimetic or a fragment amino acid sequence can be modified as described above by substituting at least one tryptophan of the amino acid sequence with an oxidant resistant amino acid.

"Biologically effective amounts" or "therapeutically effective amounts" in terms of each of the foregoing therapeutic methods are therefore amounts of the at least one modified ApoA1 polypeptide or a fragment thereof effective to exert an anti-inflammatory effect, promotion of cellular cholesterol efflux, or amelioration of symptoms of cardiovascular disease.

"Administration", as used herein, means provision or delivery of a composition including at least one ApoA1 mimetic polypeptide or a fragment thereof in an amount(s) and for a period of time(s) effective to exert an anti-inflammatory effect, promotion of cellular cholesterol efflux, or amelioration of symptoms of cardiovascular disease. The passive administration of proteinaceous therapeutics is generally preferred, in part, for its simplicity and reproducibility.

Due to the oxidation resistant properties of the polypeptides of the present invention, the ApoA1 mimetic polypeptides and fragments thereof described herein can also be used in a method of promoting cholesterol efflux from a cell to the liver. The method includes the step of administering to the cell a biologically effective amount of purified polypeptide having an amino acid sequence corresponding to a portion of SEQ ID NO:1, wherein X is selected from the group consisting of tryptophan or phenylalanine and at least one X is phenylalanine.

The present invention further relates to a method of ameliorating one or more symptoms of an inflammatory condition in a subject. The term "ameliorating" when used with respect to "ameliorating one or more symptoms of an inflammatory condition" refers to a reduction, prevention, or elimination of one or more symptoms characteristic of an inflammatory condition and/or associated pathologies. Such a reduction includes, but is not limited to a decrease in inflammatory protein biosynthesis, reduction in plasma cholesterol, and the like. The method includes the step of administering to the subject a pharmaceutical composition comprising an ApoA1 mimetic or fragment thereof. The treatment of both chronic and acute inflammatory conditions are contemplated by the present invention.

Yet another aspect of the present invention relates to a method of promoting wound healing and/or treating or ameliorating endothelial injury, e.g., arterial endothelial cell injury, which can occur after vascular injury (e.g., balloon angioplasty). The method can include the step of administering to the subject a pharmaceutical composition comprising an ApoA1 mimetic or fragment thereof to the subject. The ApoA1 mimetic or fragment thereof can be administered in an amount effective to promote endothelial cell migration and treat the endothelial cell injury.

The therapeutic methods and uses of the invention also extend to the provision of nucleic acids that encode at least one therapeutic including ApoA1 mimetic polypeptide(s) or a fragment(s) thereof in a manner effective to result in their expression in the vicinity of the targeted symptom, condition, or disease. Any gene therapy technique may be employed, such as naked DNA delivery, recombinant genes and vectors, cell-based delivery, including ex vivo manipulation of patients' cells, and the like.

It will also be understood that even in such circumstances where the dose, or combined therapy of ApoA1 polypeptides or fragments thereof, are towards the low end of the intended therapeutic range, it may be that this therapy is still equally or even more effective than all other known therapies in the context of the particular disorder or patient. It is unfortunately evident to a clinician that certain disorders and conditions cannot be effectively treated in the intermediate or long term, but that does not negate the usefulness of the present therapy, particularly where it is at least about as effective as the other strategies generally proposed.

The intention of the therapeutic regimens of the present invention is generally to produce significant anti-inflammatory effects or cholesterol efflux promotion, while still keeping the dose below the levels associated with unacceptable toxicity. In addition to varying the dose itself, the administration regimen can also be adapted to optimize the treatment strategy.

The active agents, of this invention are also useful in a number of contexts. For example, it has been observed that cardiovascular disorders (e.g., atherosclerosis, stroke, etc.) frequently accompany or follow the onset of an acute phase inflammatory response, e.g., such as that associated with a recurrent inflammatory disease, a viral infection (e.g., influenza), a bacterial infection, a fungal infection, an organ transplant, a wound or other trauma, and so forth.

Thus, in certain embodiments, this invention contemplates administering one or more of the active agents described herein to a subject at risk for, or incurring, an acute inflammatory response and/or at risk for or incurring a symptom of atherosclerosis and/or an associated pathology (e.g., stroke).

Thus, for example, a person having or at risk for coronary disease may prophylactically be administered one or more pharmaceutical compositions of this invention during flu season. A person (or animal) subject to a recurrent inflammatory condition, e.g., rheumatoid arthritis, various autoimmune diseases, etc., can be treated with a one or more agents described herein to mitigate or prevent the development of atherosclerosis or stroke. A person (or animal) subject to trauma, e.g., acute injury, tissue transplant, etc. can be treated with a polypeptide of this invention to mitigate the development of atherosclerosis or stroke. In another specific example, a subject could be treated through i.v. injections post myocardial infarction to reduce the plaque size and stabilize the plaque to prevent rupture or erosion.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

In the following examples, we sought to determine the effects of modifying lysine, methionine, and tryptophan, which are MPO sensitive residues in ApoA1. It was found that replacement of the four ApoA1 tryptophan residues with leucines leads to loss of function, while the replacement of tryptophan with phenylalanine not only preserves ApoA1 function, but renders it resistant to oxidative inactivation by MPO.

Methods

Mass Spectrometry

Human atheroma derived ApoA1 was isolated by immunoaffinity chromatography as previously described. ApoA1 was eluted in glycine buffer (pH 2.5) and subjected directly to trypsin digestion or first separated by SDS-PAGE and subjected to in gel trypsin digestion. Mass spectrometry was performed and collision-induced dissociation (CID) spectra were obtained, as previously described. Chlorotyrosine and 2-amino adipic acid analysis were performed after acid hydrolysis with heavy isotope internal standards as previously described using duplicate assays of ApoA1 from human atheroma or from plasma of healthy volunteers isolated by immunoaffinity chromatography.

Site-Directed Mutagenesis and Recombinant ApoA1 Production

Point mutations to tryptophan (8, 50, 72, 108) and methionine (86, 112, 148) residues were made using QuickChange Mutagenesis Kit from Stratagene and confirmed by DNA sequencing. Plasmids were transformed into *Escherichia coli* strain BL21 (DE-3) pLysS, InJ ApoA1 expression and purification was performed as described previously. rh-ApoA1 was extensively dialyzed against PBS or MPO reaction buffer (60 mmol/L sodium phosphate, 100 mmol/L sodium chloride, 100 μmol/L diethylenetriamine pentaacetic acid, pH 7.0) to remove any trace of imidazole, analyzed by SDS-PAGE, and found to be >95% pure. Because Trp and Met substitution alters the protein $OD_{280}$ and reactivity to the BCA or Lowry protein assays, protein concentrations were determined based on free amines using the o-phthaldialdehyde (OPA) assay, with a human plasma-derived ApoA1 (Biodesign) standard, as previously described. Cleavage of the initial Met and His tag of rh-ApoA1 was performed by formic acid treatment, followed by fast protein liquid (FPLC) purification.

ApoA1 Lysine Modifications

Human plasma-derived ApoA1 was dialyzed against PBS and diluted to 0.5 mg/mL. Lysine reductive methylation was performed as previously described. Extent of lysine modification was determined by the OPA assay. ApoA1 was then dialyzed against MPO reaction buffer, and the protein concentration of lysine-modified ApoA1 was determined using the BCA reagent.

ApoA1 MPO and Hypochlorous Acid Modifications

MPO at a final concentration of 57 nmol/L, prepared as previously described, was added to ApoA1 at 100 μg/mL (3.5 μmol/L) that had been extensively dialyzed against MPO reaction buffer. The reaction was initiated by adding hydrogen peroxide at varying mole ratios to ApoA1 in 4 aliquots at 15-minute intervals at 37° C., and continuing the incubation for 90 minutes, at which time 2 mmol/L L-methionine was added to quench the reaction. For chemical modification of ApoA1, sodium hypochlorite (NaOCl) was added to 100 μg/mL ApoA1 in MPO buffer at varying concentrations in 4 aliquots at 15 minutes intervals at 37° C. After a total incubation time of 60 minutes, 2 mmol/L L-metbionine was added to quench the reaction.

ABCA I-Dependent Cholesterol Efflux Assay

RAW 264.7 murine macrophage cells were labeled with [3H] cholesterol and treated with 0.3 mmol/L 8Br-cAMP to induce ABCA1 activity, as previously described. The cells were washed and chased for 4 hours in serum-free medium in the presence of 0.3 mmol/L 8Br-cAMP and the presence or absence of various ApoA1 preparations. The radioactivity in the chase media was determined after brief centrifugation to pellet debris. Radioactivity in the cells was determined by extraction in hexane:isopropanol (3:2) with the solvent evaporated in a scintillation vial prior to counting. The percent cholesterol efflux was calculated as 100×(medium dpm)/(medium dpm+cell dpm).

Lipid Binding Activity Assay

Lipid binding activity of ApoA1 was assessed via the inhibition of phospholipase C(PLC)-mediated aggregation of human low density lipoprotein, performed as previously described. We have previously shown that this assay give results similar to those observed by the DMPC dispersion clearance assay, but it is more sensitive and requires less ApoA1. The final concentration of apoA1 used in this assay as 12.5 μg/mL. which was sufficient to decrease the initial rate LDL aggregation by ≈75%.

Detection of ApoA1 Cross Links 250 ng of ApoA1 per lane was denatured in an SDS sample buffer, run on a 10% Tris glycine gel in the presence of SDS, and the protein was transferred to a polyvinylidene fluoride (PVDF) membrane. The membrane was probed sequentially with goat anti-human ApoA1 primary antibody (1:1,000 dilution. DiaSorin) and rabbit antigoat HRP conjugated antibody (1:1,000 dilution), and ApoA1 was visualized with an enhanced chemiluminescent substrate.

Results

ApoA1 Modifications in Human Atheroma

Figure 1D:
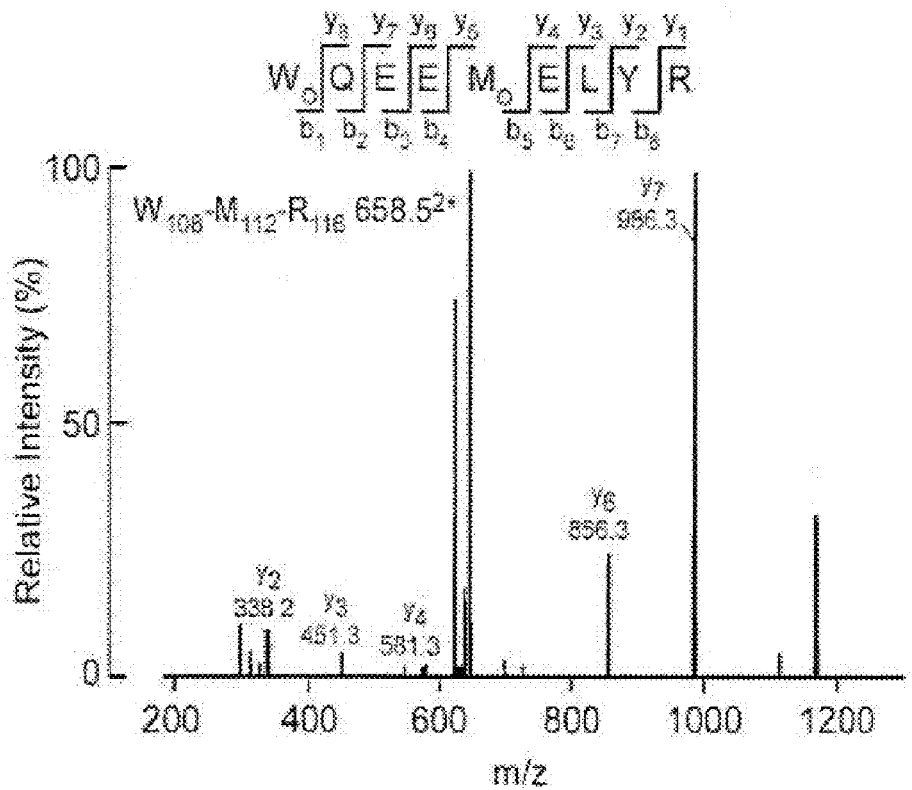
Figure 1E:
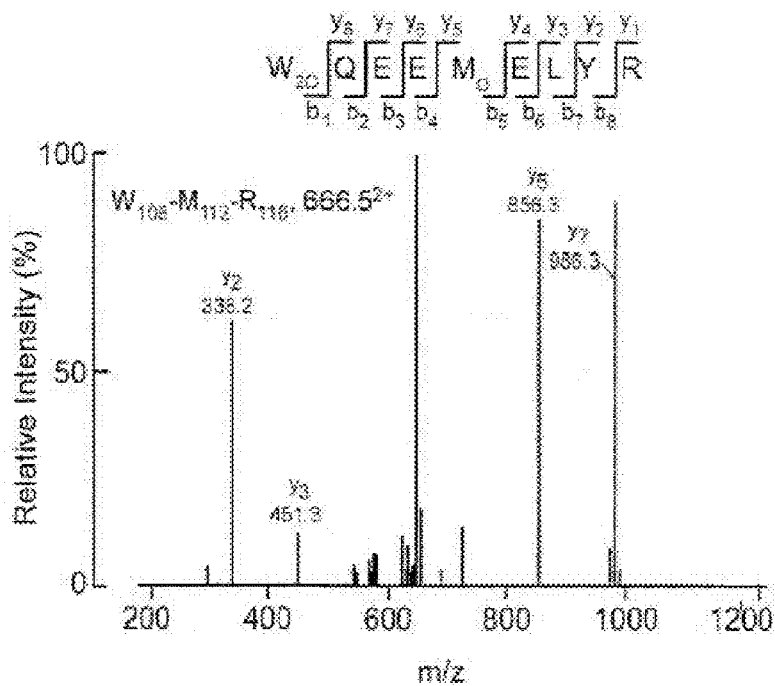
Figure 1F:
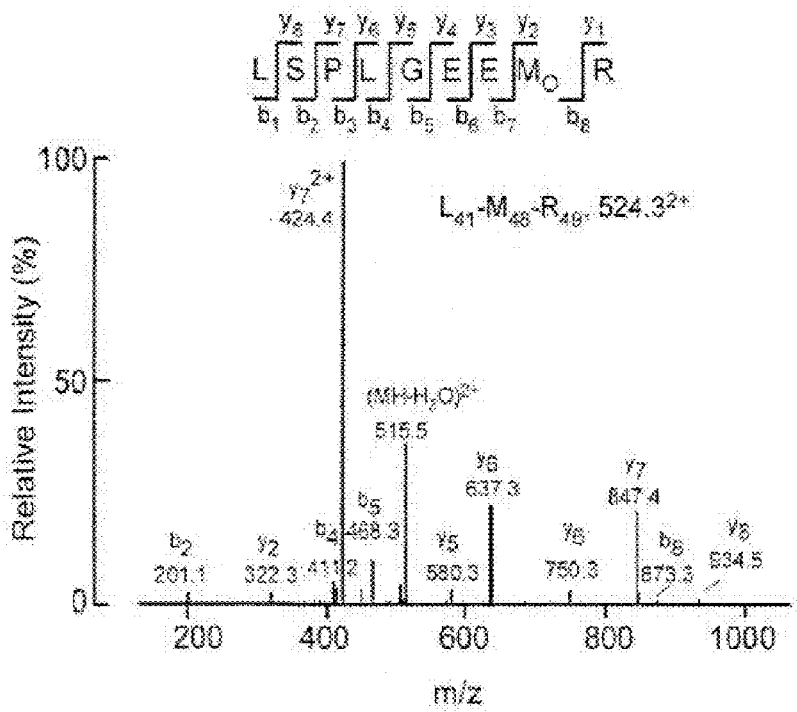
Figure 2:
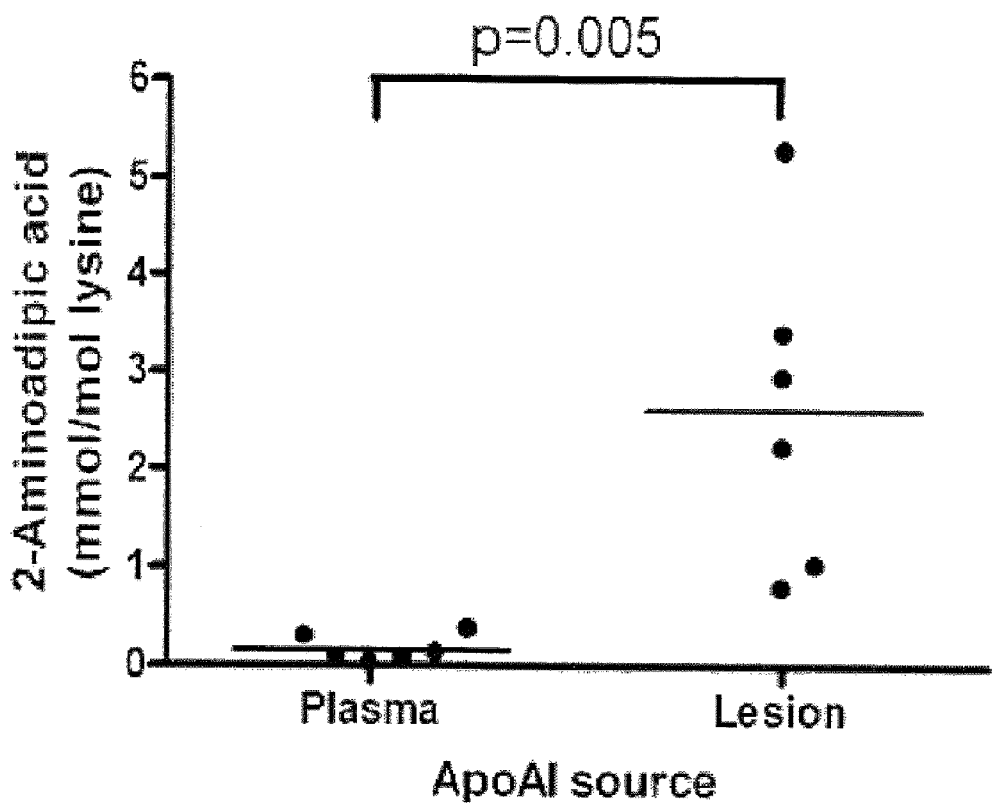
FIG. 2 illustrates a graph of lysine modification on ApoA1 isolated from human plasma and human atheroma tissue. ApoA1 was isolated by immunoaffinity chromatography from the plasma of six healthy subjects and from six atheroma samples. 2-aminoadipic acid levels, an end product of lysine modification, were quantified by mass spectrometry after acid hydrolysis, and normalized to ApoA1 lysine content. Data show mean of duplicate determinations for each sample (p=0.005 by two tailed t-test)

We determined whether ApoA1 isolated from human atheroma cells included modified tryptophan, methionine, and lysine residues Using tandem mass spectrometry, we were able to detect monohydroxytryptophan residues at all four tryptophan positions, 8, 50, 72, and 108, and dihydroxytryptophan at position 108 within apoA1 (FIGS. 1A-F). We previously identified mono- and di-hydroxytrytophan at residue W72 in in vitro MPO modified apoA1 (Peng, D. Q., Wu, Z., Brubaker, G., Zheng, L., Settle, M., Gross, E., Kinter, M., Hazen, S. L. and Smith, J. D. (2005) J Biol Chem 280, 33775-33784). In addition we detected methionine sulfoxide at residues 48 and 112 (FIG. 1D, E). To look for lysine modification by MPO-generated HOCl we used stable isotope dilution HPLC with online tandem mass spectrometry to quantify 2-aminoadipic acid, an end product of lysine oxidation by the MPO generated oxidant. 2-Aminoadipic acid levels were low but detectable in ApoA1 isolated from the plasma of six healthy volunteers, while the mean levels were strikingly elevated ~16-fold in ApoA1 isolated from six human atheroma samples (FIG. 2, p=0.005 by a two-tailed t-test). Thus, tryptophan, methionine, and lysine oxidation of ApoA1 occur physiologically within human atheroma. We therefore sought to determine which of these modifications was responsible for yielding dysfunctional ApoA1 with a diminished capacity to accept cellular cholesterol.

ApoA1 Lysine Modification

Figure 3:
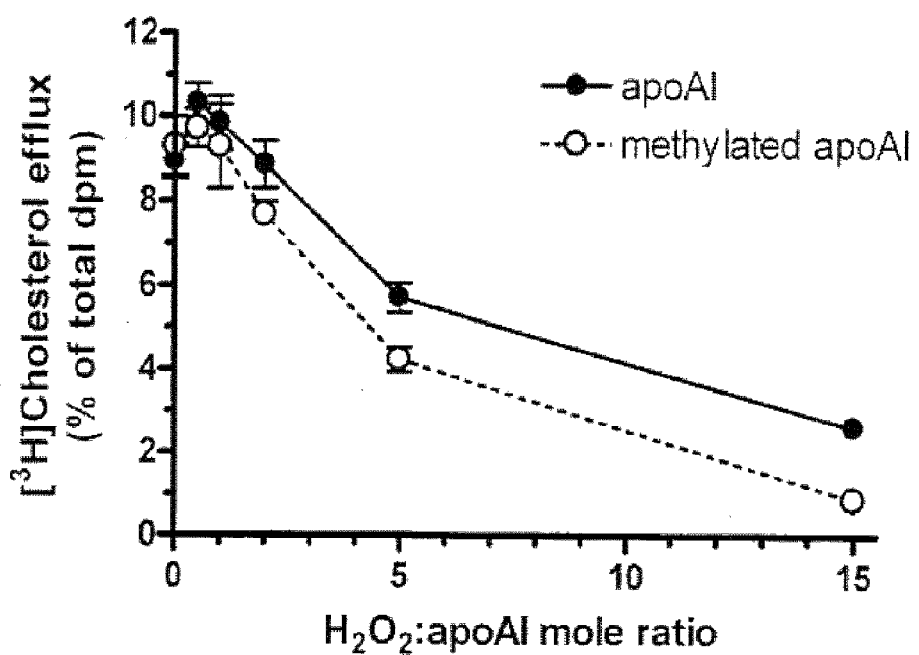
FIG. 3 illustrates plots that show protection of lysine residues by reductive methylation does not protect it from inactivation by the complete MPO/$H_2O_2$/$Cl^-$ system. ApoA1 (filled circles, solid line) and reductively methylated ApoA1 (open circles, dashed line) were subjected to modification by MPO at varying $H_2O_2$:ApoA1 mole ratios. These proteins were then assayed for ABCA1 dependent cellular cholesterol acceptor activity during a 4 hr incubation at 5 µg/ml with cholesterol labeled RAW264.7 cells, which had been treated with 0.3 mM 8Br-cAMP to induce ABCA1. Data are means±S.D. of triplicate determinations, when no bars appear, the S.D. is within the symbol.

In the amphipathic structure of ApoA1, the 21 lysine residues overwhelming reside on both sides of and adjacent to the hydrophobic face. Lysine modification by MPO is an attractive candidate to be responsible for MPO induced loss of ApoA1 function as we previously demonstrated that ApoA1 lysine residues can undergo modification by MPO, and that extensive chemical modification of ApoA1 lysine residues that alter its positive charge led to loss of ApoA1 cholesterol acceptor activity. However, we also found that lysine modification by reductive methylation, which retains the lysine positive charge, led to only modest reductions of ApoA1 function. ApoA1 was subjected to reductive methylation, leading to 92% lysine modification, or control incubation and dialyzed extensively against MPO reaction buffer. Modification reactions were performed using catalytic amounts of MPO and increasing molar ratios of $H_2O_2$:ApoA1. The reaction products were assayed for cholesterol acceptor activity using cholesterol labeled RAW264 macrophages that had been pretreated with a cAMP analogue to induce ABCA1. In the absence of $H_2O_2$ in the modification reaction, the methylated and non-methylated control ApoA1 had robust and equivalent ABCA1-dependent cholesterol acceptor activity. With increasing doses of $H_2O_2$, the cholesterol acceptor activity of both the methylated and control ApoA1 samples declined in a similar fashion (FIG. 3). In addition, the alpha helix content of these preparations was estimated by CD, and both methylated and control ApoA1 preparations were similarly susceptible to the MPO/H2O2 dose dependent reduction in alpha helix content. Since reductive methylation of lysine's primary amine into a tertiary amine decreases its chemical reactivity but did not lead to protection of ApoA1's unction, ApoA1 lysine modification by MPO is unlikely to be responsible for ApoA1's loss of function.

Methionine Modification does not Protect Against MPO Induced Loss of ApoA1 Function.

Figure 4A:
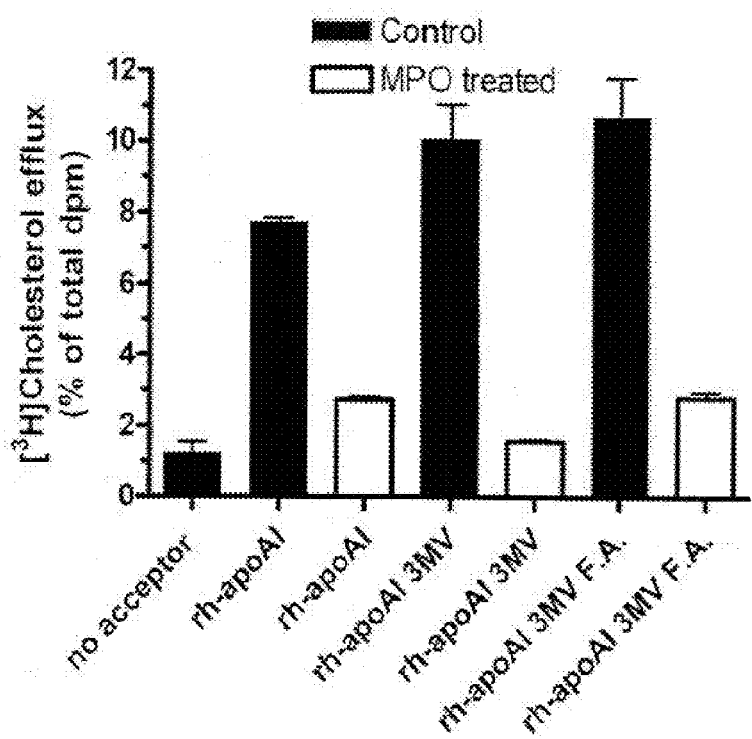
FIGS. 4(A-B) illustrate a graph (A) and plot (B) that show methionine to valine substituted ApoA1 has increased susceptibility to MPO mediated loss of function. A. High dose MPO modification, at an $H_2O_2$:ApoA1 mole ratio of 15:1, was performed on recombinant human ApoA1 (rh-ApoA1), rh-ApoA1 3MV (3 internal Met substituted with Val), and rh-ApoA1 3MV treated with formic acid (rh-ApoA1 3MV F.A.), which deletes the initiation Met and 6-His tag from the recombinant protein. Cellular cholesterol efflux activity was determined as described in FIG. 1. Data are mean±S.D. of duplicate determinations. B. rh-ApoA1 (filled circles, solid line) and rh-ApoA1 3MV (open circles, dashed line) were subjected to modification by MPO at varying $H_2O_2$: ApoA1 mole ratios. These proteins were then assayed for ABCA1 dependent cellular cholesterol acceptor activity as described in FIG. 3. Data are means±S.D. of triplicate determinations. *, p<0.01 vs. rh-ApoA1 3MV at the same $H_2O_2$:ApoA1 mole ratio, by two tailed t-test.
Figure 4B:
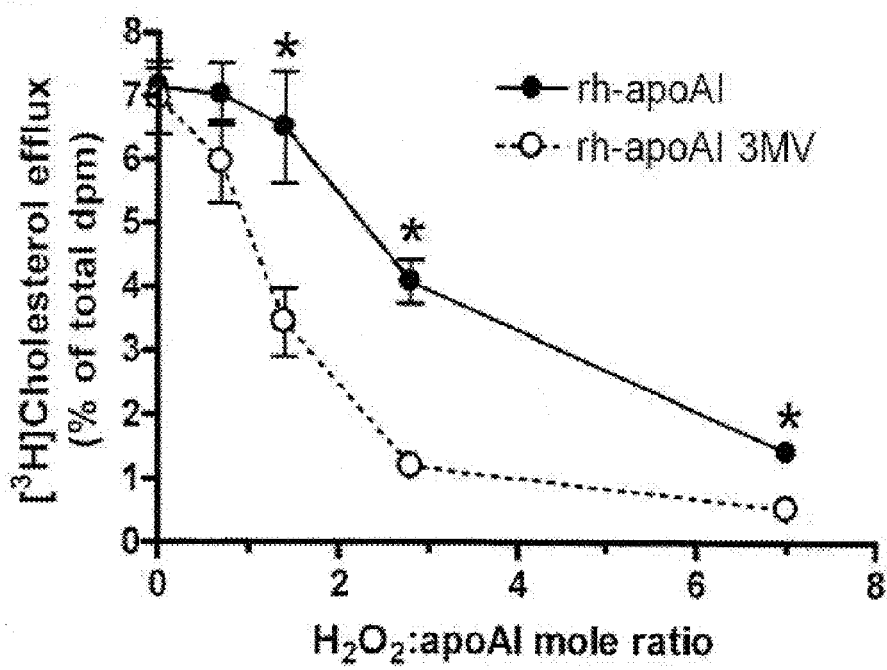

We then turned our attention to the three ApoA1 methionine residues, which were previously implicated in the MPO induced loss of ApoA1 function. In order to substitute valine for all three methionines, we used recombinant human ApoA1 (rh-ApoA1), which adds an additional methionine initiation codon and a 6-his tag to the N-terminus. We had previously demonstrated that rh-ApoA1 behaves similar to plasma derived ApoA1 in its cholesterol activity in its cholesterol acceptor activity, lipid binding activity, and its susceptibility to MPO mediated loss of function. Using site directed mutagenesis, we created an ApoA1 expression construction encoding a protein with the three internal methionines converted to valines, which we refer to as rh-ApoA1 3MV (3 methionine to valine). One cannot substitute for the initiating methionine. However, this methionine and the his tag can be chemically cleaved by formic acid incubation, as previously described (Ryan, R. O., Forte, T. M., and Oda, M. N. (2003) Protein Expr. Purif. 27, 98-103), due to the substitution of glutamate at position 2 with an aspartate, yielding a unique formic acid sensitive Asp-Pro dipeptide adjacent to the his tag. We determined that the rh-ApoA1 3MV, regardless of whether the initiating Met and His tag were intact or removed, had similar ABCA1-dependent cholesterol acceptor activity compared to wild type rh-ApoA1. In addition, the rh-ApoA1 3MV, with or without the N-terminal methionine, and wild type rh-ApoA1 were equally susceptible to a high dose ($H_2O_2$:apoA1=15:1) MPO mediated loss of cholesterol acceptor activity (FIG. 4A). MPO modifications of rh-ApoA1 and the 3MV variant were performed at varying and modest molar ratios of $H_2O_2$:ApoA1, and the 3MV variant was more sensitive to loss of cholesterol acceptor activity at low molar ratios (FIG. 4B). For example, at an $H_2O_2$:ApoA1 ratio of 1.4, wild type ApoA1 had a negligible loss of cholesterol acceptor activity, while the 3MV variant lost about half of its cholesterol acceptor activity. Thus, we found that the three methionine residues in ApoA1, instead of playing a role in oxidative impairment of ApoA1 function, actually play a protective role by harmlessly absorbing oxidants.

ApoA1 Tryptophan Residues Play a Role in ApoA1 Function.

We examined the role of ApoA1 tryptophan residues next by altering each of the four tryptophan residues to either leucine (rh-ApoA1 4WL) or phenylalanine (rh-ApoA1 4WF). The aromatic nature of the tryptophan residues seemed to be crucial for ApoA1's cholesterol acceptor activity, as the 4WL variant lost the majority of this activity in cholesterol efflux studies carried out over a wide range of ApoA1 doses, while the 4WF variant retained this activity (FIG. 5A). We examined the predicted alpha helix content of these proteins by CD using the K2d algorithm, and found that the wild type protein had 57% alpha helix, while the 4WL and 4WF variants both had increased alpha helix contents of 79% and 77%, respectively. Thus, the loss of efflux and lipid binding activity of the 4WL variant cannot be attributed to loss of helical content.

Both rh-ApoA1 and the 4WF variant were subjected to the MPO/CL$^-$/$H_2O_2$ oxidation system at increasing doses of $H_2O_2$. FIG. 5B shows the result of a study representative of 4 different experiments using two independent preparations of each protein. As previously observed, the ABCA1-dependent cholesterol acceptor activity of wild type ApoA1 was inhibited by increasing MPO induced oxidation; however, the 4WF variant maintained this activity even at an $H_2O_2$:ApoA1 ratio of 15.

Figure 6:
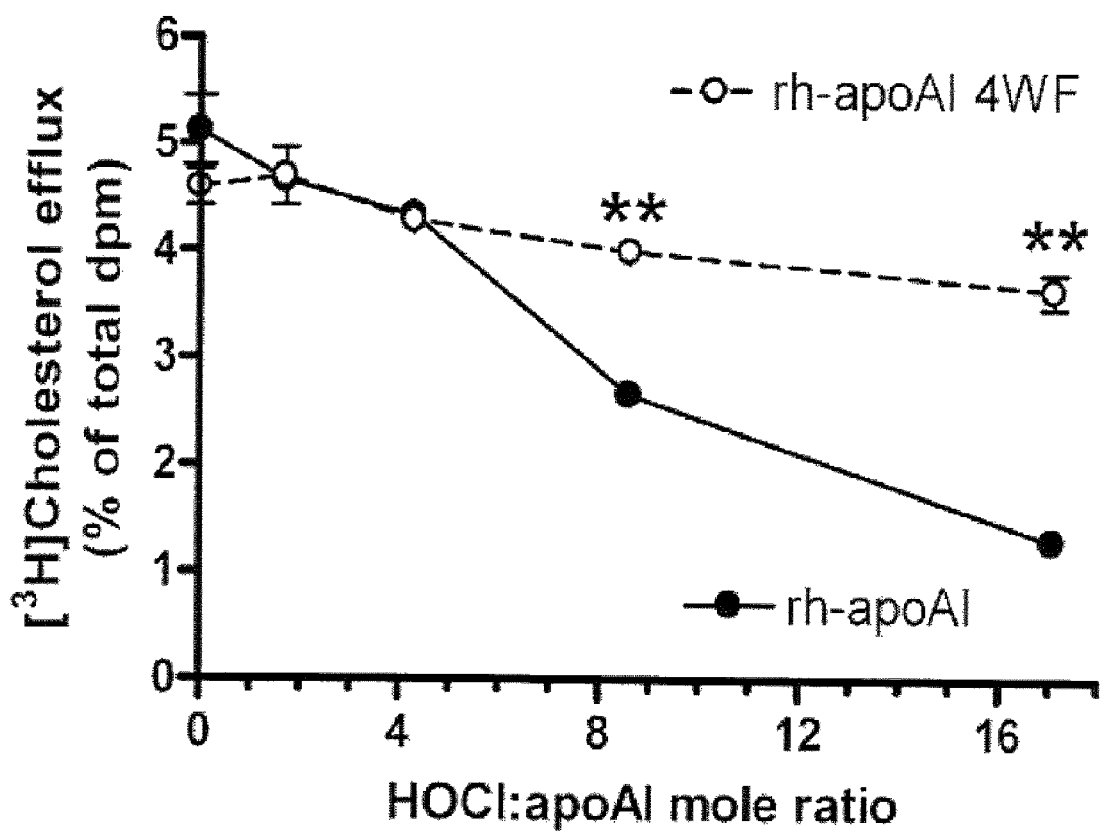
FIG. 6 illustrates a plot showing tryptophan to phenylalanine substituted ApoA1 is resistant to HOCl mediated loss of function. rh-ApoA1 (filled circles, solid line) and rh-ApoA1 4WF (open circles, dashed line) were subjected to modification at varying HOCl:ApoA1 mole ratios. These proteins were then assayed for ABCA1 dependent cellular cholesterol acceptor activity as described in FIG. 3. Data are means±S.D. of triplicate determinations. **, p<0.0001 vs. rh-ApoA1 at the same HOCl:ApoA1 mole ratio, respectively, by two tailed t-test.

The MPO/Cl$^-$/$H_2O_2$ oxidation system generates HOCl, the active reagent of bleach, and we and others have previously demonstrated that HOCl treatment of ApoA1 results in loss of cholesterol acceptor and lipid binding activity. Thus, we subjected wild type ApoA1 and the 4WF variant to increasing doses of HOCl. Similar to the findings with the MPO modification system, the cholesterol acceptor activity of the 4WF variant was resistant to this treatment while the efflux activity of wild type rh-ApoA1 was impaired by increasing doses of HOCl (FIG. 6).

The lipid binding activity of rh-ApoA1 and the 4WF variant were assessed by a DMPC emulsion clearance assay, and both proteins showed equivalent activity (FIG. 7A). The cell free lipid binding activity of rh-ApoA1 4WF was also resistant to MPO mediated inhibition, compared to rh-ApoA1 (FIG. 4B) using a PLC mediated LDL aggregation assay (FIG. 7B).

Figure 8:
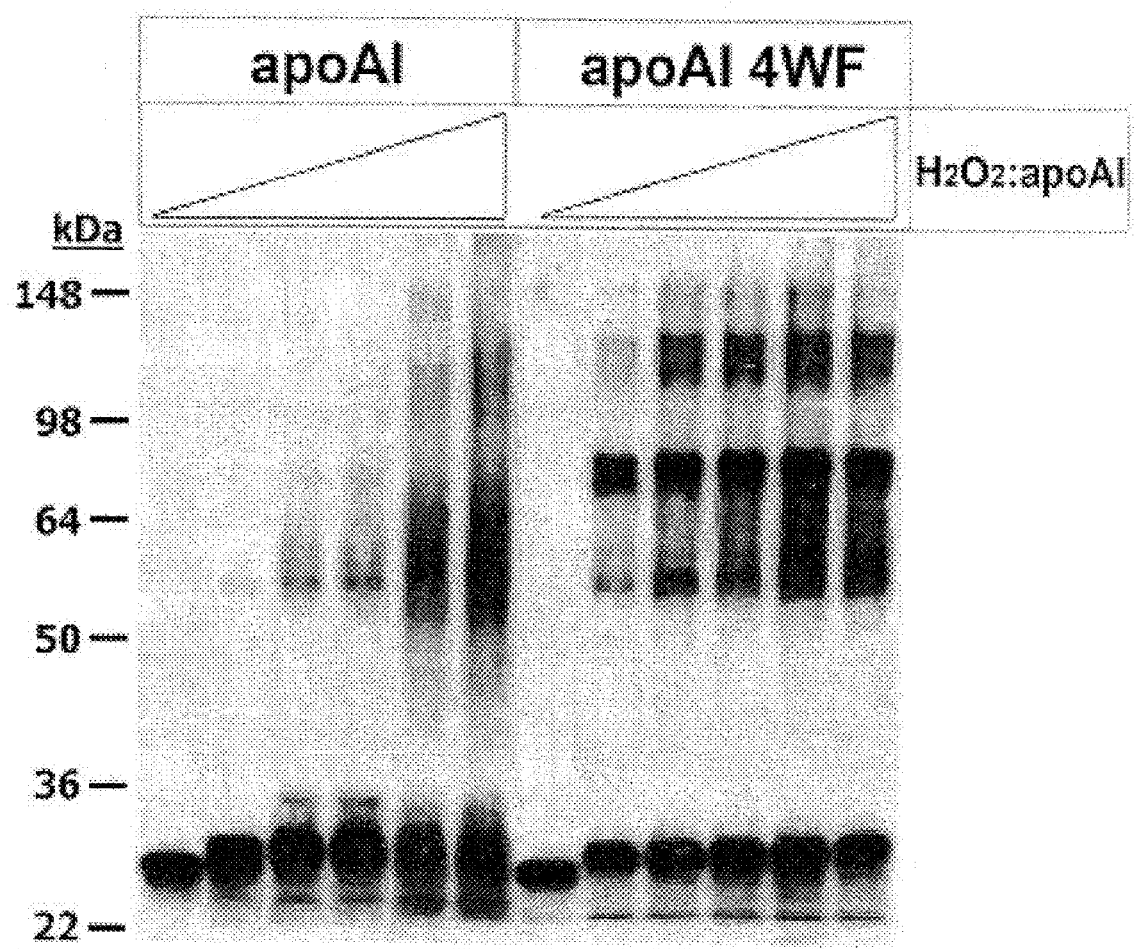
FIG. 8 illustrates an immunoblot showing tryptophan to phenylalanine substituted ApoA1 is still susceptible to cross linking by MPO. rh-ApoA1, and rh-ApoA1 4WF were subjected to MPO modification at the following mole ratios of $H_2O_2$:ApoA1; 0, 1, 2, 3, 5, and 12.5 (from left to right). ApoA1 cross linking was qualitatively assessed by Western blotting. The migration of molecular weight standards is shown on the left side.

MPO modification of ApoA1 leads to extensive cross linking resulting in dimers, multimers, and presumably intramolecular cross links as well. We previously have shown that the MPO mediated ApoA1 cross linking pattern was not altered in the variant with all 7 tyrosine residues converted to phenylalanine. Upon subjecting rh-ApoA1 and the 4WF variant to MPO/Cl$^-$/$H_2O_2$ oxidation at increasing doses of $H_2O_2$ (using the identical protein products that were used for efflux in FIG. 5B), we observed altered migration of both proteins in denaturing gels consistent with intermolecular cross-linking. However, the migration patterns were different, with the 4WF variant giving a sharp predominant band at about 70 kD, while the wild type protein yielded a less distinct predominant zone between 55 and 65 kD (FIG. 8). The migration of the monomer was altered for both proteins, which could be indicative of intramolecular cross-links or amino acid modifications. Although the 4WF variant is resistant to MPO mediated loss of cholesterol acceptor activity, this variant was more susceptible to MPO induced cross-linking, particularly at low doses of $H_2O_2$. We also subjected these modified proteins to structural analysis by CD, and found that both were susceptible to loss of alpha helical content, although the 4WF variant started with a higher value.

Figure 9:
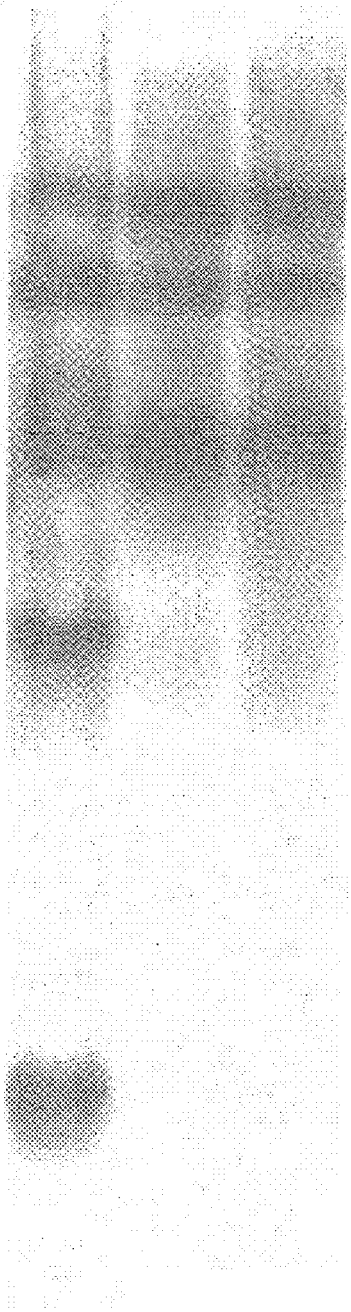
FIG. 9 illustrates a gradient gel showing migration of lipid free rh-ApoA1. A. rHDL was prepared by cholate dialysis using palmitoyl oleoyl phosphatidylcholine (POPC) and wild type or 4WF rh-ApoA1 (00:1 molar ratio POPC:apoA1) and run on 4-20% non-denaturing gradient polyacrylamide gels. Lane 1, size standards with diameters listed to left; lane 2, 10 μg wild type rh-ApoA1 rHDL; lane 3, 10 μg 4WF rh-apoA1 rHDL. Both ApoA1 variants yielded ~9.8, 12, and 17 nm discs on non-denaturing gradient gels. The migration of lipid free rh-ApoA1 is shown by the arrow on the right side.
Figure 10:
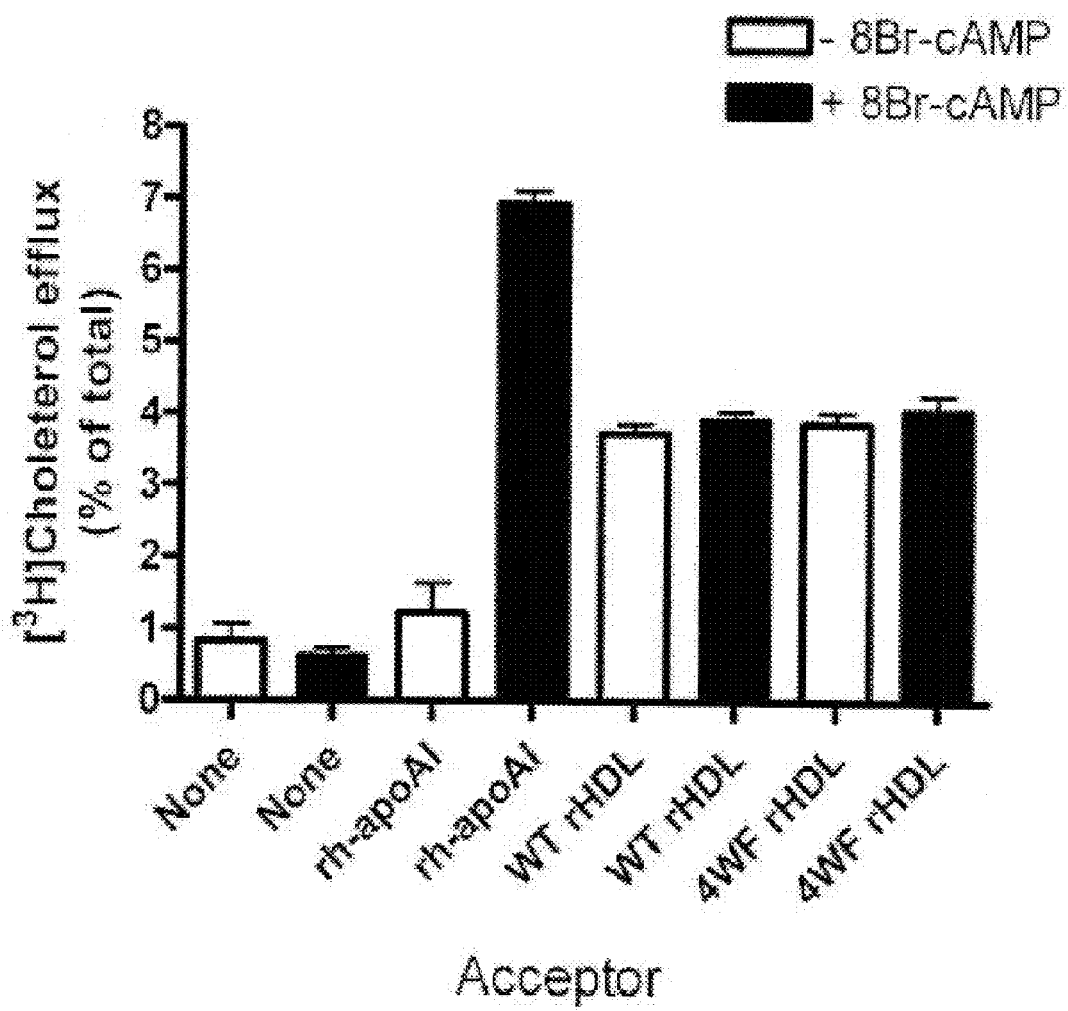
FIG. 10 illustrates a graph showing cholesterol efflux activity of rHDL preparations (4 hr. incubation) from [3H] cholesterol labeled RAW264.7 cells in the presence (filled bars) or absence (open bars) of ABCA 1 induction by pretreatment with 0.3 mM 8Br-cAMP. rh-ApoA1 (10 μg/ml) yielded ABCA1 dependent cholesterol acceptor activity; however, both the wild type (WT) and 4WF ApoA1 rHDL preparations (10 μg/ml ApoA1) yielded only ABCA 1 dependent cholesterol acceptor activity. Bars show mean±S.D. (n=3).

We also prepared rHDL by cholate dialysis using POCP and the wild type or 4WF ApoA1. Both yielded a similar pattern of rHDL discs estimated by non-denaturing gels at ~9.8, 12, and 17 nm, without any lipid free ApoA1 remaining (FIG. 9). We tested the wild type and 4WF rHDL, and both were equally competent to mediate ABCA1-independent cholesterol efflux from RAW264.7 cells (FIG. 10), without ABCA1 dependent acceptor activity, as expected for fully lipidated ApoA1.

Figure 11:
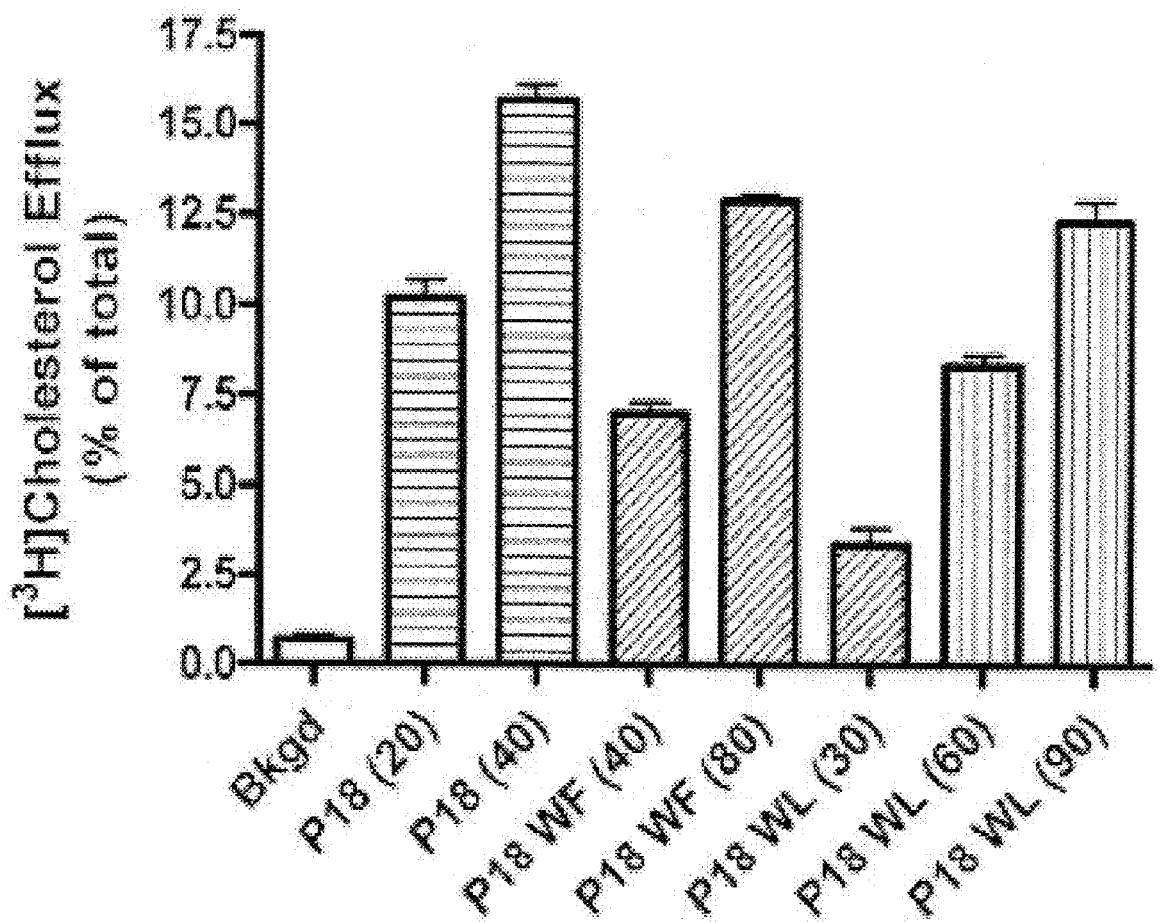
FIG. 11 illustrates a graph showing the ABCA1-dependent cholesterol acceptor activity of synthetic peptides with tryptophan substitutions. The parent peptide p18 (Ac-DW-FKAFYDKVAEKFKEAF-NH$_2$) (SEQ ID NO:76) was synthesized with or without substitution of the tryptophan residue (W) for phenylalanine (p18 WF) or leucine (p8WL). The cholesterol acceptor activity of the three peptides were measured by 4 hour incubation with [$^3$H] cholesterol labeled RAW264.7 cells that had been pretreated with 0.3 mM 8Br-cAMP to induce ABCA1. The concentration of peptide is shown in, μg/ml in the column labels. Bars show mean±S.D. (n=3).

We synthesized the previously described helical amphiathic peptide p18, which contains a tryptophan residue at position 2. We also synthesized analogues replacing the tryptophan with phenylalanine (P18 WF) or leucine (P18 LF). We demonstrated that this tryptophan-free peptides have dose dependent ABCA1-mediated cholesterol acceptor activity (FIG. 11).

From the above description of the invention, those skilled in the art will perceive improvements, changes and modifications. Such improvements, changes and modifications within the skill of the art are intended to be covered by the appended claims. Al references, publications, and patents cited in the present application are herein incorporated by reference in their entirety.

Having described the invention, the following is claimed:

1. An isolated polypeptide consisting of the amino acid sequence of SEQ ID NO:1, in which each X in SEQ ID NO:1 is a phenylalanine amino acid.

2. The polypeptide of claim 1, wherein said polypeptide is a purified polypeptide.

3. The polypeptide of claim 1, wherein said polypeptide is a recombinant polypeptide.

4. The polypeptide of claim 3, wherein said polypeptide is a recombinant polypeptide produced in bacteria, yeast, plant, insect, avian, or mammalian cells.

5. The polypeptide of claim 1, wherein said polypeptide is resistant to at least one of oxidation by myeloperoxidase (MPO), oxidation by nitrogen dioxide, oxidation by peroxynitrite (ONOO$^-$), oxidation by peroxycarboxynitrite (ONOOCO$_2^-$), or oxidation by a product formed when ONOO$^-$ acts in presence of $CO_2$ or $HCO_3^-$ in buffer.

6. The polypeptide of claim 5, wherein oxidation by myeloperoxidase (MPO) comprises, MPO generated oxidant, oxidation by an MPO-generated reactive chlorinating species, oxidation associated with the MPO/$H_2O_2$/Cl$^-$ system, oxidation by MPO generated HOCl/OCl$^-$, oxidation by a MPO generated reactive nitrogen species, or oxidation associated with the MPO/$H_2O_2$/$NO_2^-$ system.

7. The polypeptide of claim 1, wherein said polypeptide is resistant to oxidation by MPO.

8. The polypeptide of claim 1, wherein said polypeptide further comprises a polyhistidine-tag.

9. A pharmaceutical composition comprising a polypeptide and a pharmaceutically acceptable excipient, wherein said polypeptide consists of the amino acid sequence of SEQ ID NO:1, in which each X in SEQ ID NO:1 is a phenylalanine amino acid.

10. The pharmaceutical composition of claim 9, wherein the polypeptide is a purified polypeptide.

11. The pharmaceutical composition of claim 9, wherein the composition is formulated for administration to a subject by a route selected from the group consisting of oral administration, nasal administration, rectal administration, intraperitoneal injection, intravascular injection, subcutaneous injection, transcutaneous administration, inhalation administration, and intramuscular injection.

12. The pharmaceutical composition of claim 11, wherein said composition is formulated as a unit dosage formulation.

13. The pharmaceutical composition of claim 11, wherein the pharmaceutical composition is formulated for intravascular administration.

14. The pharmaceutical composition of claim 11, wherein the pharmaceutical composition comprises a powdered form of the polypeptide and a vehicle.

15. The pharmaceutical composition of claim 14, wherein the vehicle comprises sterile pyrogen free water, buffer, or dextrose solution.

16. The pharmaceutical composition of claim 14, wherein the powdered form of the polypeptide comprises lyophilized powdered polypeptide.

17. The pharmaceutical composition of claim 11, wherein the pharmaceutical composition is formulated for subcutaneous injection, transcutaneous administration, or intramuscular injection.

18. The pharmaceutical composition of claim 17, wherein the pharmaceutical composition comprises polymeric, hydrophobic materials, or ion exchange resins.

* * * * *